(12) United States Patent
Gupta et al.

(10) Patent No.: US 11,596,364 B2
(45) Date of Patent: Mar. 7, 2023

(54) METHOD AND SYSTEM FOR DETECTING EVENTS IN AN INPUT SIGNAL USING VOLATILE MEMRISTOR STATE CHANGE

(71) Applicant: UNIVERSITY OF SOUTHAMPTON, Southampton (GB)

(72) Inventors: Isha Gupta, Southampton (GB); Alexantrou Serb, Southampton (GB); Themistoklis Prodromakis, Southampton (GB)

(73) Assignee: UNIVERSITY OF SOUTHAMPTON, Southampton (GB)

(*) Notice: Subject to any disclaimer, the term of this patent is extended or adjusted under 35 U.S.C. 154(b) by 908 days.

(21) Appl. No.: 16/349,107

(22) PCT Filed: Oct. 16, 2017

(86) PCT No.: PCT/GB2017/053119
§ 371 (c)(1),
(2) Date: May 10, 2019

(87) PCT Pub. No.: WO2018/087515
PCT Pub. Date: May 17, 2018

(65) Prior Publication Data
US 2019/0269372 A1 Sep. 5, 2019

(30) Foreign Application Priority Data
Nov. 11, 2016 (GB) ...................................... 1619154

(51) Int. Cl.
*G11C 13/00* (2006.01)
*A61B 5/00* (2006.01)
*G11C 11/54* (2006.01)
*G06N 3/06* (2006.01)
*A61B 5/24* (2021.01)

(52) U.S. Cl.
CPC .............. *A61B 5/7282* (2013.01); *A61B 5/24* (2021.01); *G06N 3/061* (2013.01); *G11C 11/54* (2013.01); *G11C 13/004* (2013.01); *G11C 13/0007* (2013.01); *G11C 13/0069* (2013.01); *A61B 5/4064* (2013.01)

(58) Field of Classification Search
CPC ... G11C 11/54; G11C 13/0007; G11C 13/004; G11C 13/0069
See application file for complete search history.

(56) References Cited

U.S. PATENT DOCUMENTS

| | | | |
|---|---|---|---|
| 10,082,565 B2* | 9/2018 | Chen | G01S 7/5202 |
| 10,270,676 B2* | 4/2019 | Shirakawa | H04L 43/12 |
| 10,288,426 B2* | 5/2019 | Aoyama | G01D 3/08 |

(Continued)

OTHER PUBLICATIONS

Al-Shedivat et al., "Memristors Empower Spiking Neurons with Stochasticity," IEEE Journal on Emerging and Selected Topics in Circuits and Systems, vol. 5, No. 2 (Jun. 2015).

(Continued)

*Primary Examiner* — Hien N Nguyen
(74) *Attorney, Agent, or Firm* — Volpe Koenig

(57) ABSTRACT

The present invention provides a method for detecting events in an input signal. The method uses a volatile resistive switching component to detect the events in the input signal. The method comprising identifying the events based on sampling an output from the resistive switching component.

16 Claims, 11 Drawing Sheets

(56) References Cited

U.S. PATENT DOCUMENTS

2012/0011092 A1 1/2012 Tang et al.
2015/0006455 A1 1/2015 Suri et al.

OTHER PUBLICATIONS

Baranauskas, "What Limits the Performance of Current Invasive Brain Machine Interfaces," Frontiers in Systems Neuroscience, vol. 8, Article 68, pp. 1-10 (Jan. 2014).
Berdan et al., "Emulating Short-Term Synaptic Dynamics with Memristive Devices," Scientific Reports, pp. 1-9 (2016).
Berdan et al., "Supplementary Information, Emulating short-term synaptic dynamics with memristive devices," Sci. Rep. 6 (2016).
Berdan et al., "Temporal Processing with Volatile Memristors," IEEE International Symposium on Circuits and Systems (May 2013).
Blanche et al., "Polytrodes: High-Density Silicon Electrode Arrays for Large-Scale Multiunit Recording," Journal of Neurophysiology, vol. 93, pp. 2987-3000 (2005).
Buzsaki, "Large-Scale Recording of Neuronal Ensembles," Nature Neuroscience, vol. 7, No. 5, pp. 446-451 (May 2004).
Chua et al., "Memristive Devices and Systems," Proceedings of the IEEE, vol. 64, No. 2 (Feb. 1976).
Cortese et al., "A $TiO_2$-based Volatile Threshold Switching Selector Device with $10^7$ non linearity and sub 100 pA Off Current," International Symposium on VLSI Technology, Systems and Application (2016).
Cortese et al., "On the Origin of Resistive Switching Volatility in $Ni/TiO_2/Ni$ Stacks," Jorunal of Applied Physics, vol. 120, 065104 (2016).
Eftekhar et al., "Towards a Next Generation Neural Interface: Optimizing Power, Bandwidth and Data Quality," pp. 122-125 (2010).
Eversmann et al., "A 128×128 CMOS Biosensor Array for Extracellular Recording of Neural Activity," IEEE Journal of Solid-State Circuits, vol. 38, No. 12, pp. 2306-2317 (Dec. 2003).
Franke et al., "High-density Microelectrode Array Recordings and Real-time Spike Sorting for Closed-loop Experiments: An Emerging Technology to Study Neural Plasticity," Frontiers in Neural Circuits, pp. 1-7 (Dec. 2012).
Frey et al., "Microelectronic System for High-Resolution Mapping of Extracellular Electric Fields Applied to Brain Slices," Biosensors & Bioelectronics, vol. 24, No. 7, pp. 2191-2198 (Mar. 2009).
Gosselin, "Recent Advances in Neural Recording Microsystems," Sensors, vol. 11, pp. 4572-4597 (2011).
Gupta et al., "A Cell Classifier for RRAM Process Development," IEEE Transactions on Circuits and Systems II: Express Briefs, vol. 62, No. 7, pp. 676-680 (2015).
Gupta et al., "Improving Detection Accuracy of Memristor-Based Bio-Signal Sensing Platform," IEEE Transactions on Biomedical Circuits and Systems, pp. 203-211 (2016).
Gupta et al., "Practical Operation Considerations for Memristive Integrating Sensors," 2016 IEEE International Symposium on Circuits and Systems, pp. 2322-2325 (May 2016).
Gupta et al., "Real-Time Encoding and Compression of Neuronal Spokes by Metal-Oxide Memristors," Nature Communications, (No. 7), Article 12805 (Sep. 2016).
Gupta et al., "Sub 100 nW volatile nano-metal-oxide memristor as synaptic-like encoder of neuronal spikes," (Nov. 29, 2016).
Gupta et al., "Supplementary Information: Real-time Encoding and Compression of Neuronal Spokes by Metal-Oxide Memristors," pp. 1-10 (Sep. 2016).
Gupta et al., "Towards a Memristor-Based Spike-Sorting Platform," 2016 Biomedical Circuits and Systems Conference, pp. 408-411 (Oct. 2016).
Hajjhassen et al., "NeuroMEMS: Neural Probe Microtechnologies," Sensors, vol. 8, pp. 6704-6726 (2008).
Hatsopoulos et al., "The Science of Neural Interface Systems," Annual Review of Neuroscience, vol. 32, pp. 249-266 (2009).
Hierlemann et al., "Growing Cells Atop Microelectronic Chips: Interfacing Electrogenic Cells In Vitro with CMOS-based Microelectrode Arrays," Proceedings of the IEEE, vol. 99, No. 2, pp. 252-284 (Feb. 2011).
Homer et al., "Implants and Decoding for Intracortical Brain Computer Interfaces," Annual Review of Biomedical Engineering, vol. 15, pp. 383-405 (2013).
Jeong et al., "Emerging Memories: Resistive Switching Mechanisms and Current Status," Reports on Progress in Physics, vol. 75, No. 7 (Jul. 2012).
Khiat et al., "High Density Crossbar Arrays with Sub-15 nm Single Cells via Liftoff Process Only," Nature Scientific Reports, vol. 6, 32614 (2016).
Lambacher et al., "Identifying Firing Mammalian Neurons in Networks with High-Resolution Multi Transistor Array (MTA)," Applied Physics A 102:1-11 (Sep. 2010).
Lewicki, "A Review of Methods for Spike Sorting: the Detection and Classification of Neural Action Potentials," Network: Computation in Neural Systems, vol. 9, pp. R53-R78 (1998).
Linares-Barranco et al., "Memristance Can Explain Spike-Time-Dependent-Plasticity in Neural Synapses," Nature Precedings, pp. 1-4 (2009).
Lopez et al., "A 966-Electrode Neural Probe with 384 Configurable Channels in 0.13 µm SOI CMOS," IEEE Transactions on Biomedical Circuits and Systems, vol. 11, No. 3, pp. 510-522 (206).
Mustafa et al., "A Novel Reference Scheme for Reading Passive Resistive Crossbar Memories," IEEE Transactions on Neurotechnology, vol. 5, No. 6, pp. 687-691 (Nov. 2006).
Navarro et al., "A Critical Review of Interfaces with the Peripheral Nervous System for the Control of Neuroprotheses and Hybrid Bionic Systems," Journal of the Peripheral Nervous System, vol. 10, pp. 229-258 (2005).
Nicolas-Alonso et al., "Brain Computer Interfaces, a Review," Sensors, vol. 12, No. 2, pp. 1211-1279 (Jan. 2012).
Nicolelis et al., "Principles of Neural Ensemble Physiology Underlying the Operation of Brain-Machine Interfaces," Nature, vol. 10, pp. 530-540 (Jul. 2009).
Paraskevopoulou et al., "A Sub-1 µW Neural Spike-Peak Detection and Spike-Count Rate Encoding Circuit," IEEE Biomedical Circuits and Systems Conference, pp. 29-32 (Nov. 2011).
Pedreira et al., "How Many Neurons Can We See with Current Spike Sorting Algorithms," Journal of Neuroscience Methods, vol. 211, pp. 58-65 (2012).
Prezioso et al., "Training and Operation of an Integrated Neuromorphic Network Based on Metal-Oxide Memristors," Nature, vol. 521, pp. 61-64 (May 2015).
Prodromakis et al., "Two Centuries of Memristors," Nature Materials, vol. 11, No. 6, pp. 478-481 (Jun. 2012).
Quiroga, "Spike Sorting," Current Biology, vol. 22, R45-46 (2012).
Rey et al., "Past, Present, and Future of Spike Sorting Techniques," Brain Research Bulletin, vol. 119, pp. 10-117 (Apr. 2015).
Schmidt, "Computer Separation of Multi-Unit Neuroelectric Data: A Review," Jorunal of Neuroscience Methods, vol. 12, pp. 95-111 (1984).
Seok et al., "A Review of Three-Dimensional Resistive Switching Cross-Bar Array Memories from the Integration and Materials Property Points of View," Advanced Functional Materials, vol. 24, pp. 5316-5339 (2014).
Serb et al., "An RRAM biasing parameter optimizer," IEEE Transactions on Electronic Devices 62, pp. 3685-3691 (2015).
Serb et al., "Live Demonstration: A Versatile, Low-Cost Platform for Testing Large ReRAM Cross-Bar Arrays," IEEE International Symposium on Circuits and Systems, vol. 9, No. 5 (2014).
Serb et al., "Memristors as Synapse Emulators in the Context of Event-Based Computation," IEEE International Symposium on Circuits and Systems (Jun. 2014).
Stevenson et al., "How Advances in Neural Recording Affect Data Analysis," Nature Neurosciences, vol. 14, pp. 139-142 (2011).
Strukov et al., "Exponential Ionic Drift: Fast Switching and Low Volatility of Thin-Film Memristors," Applied Physics A, vol. 94, pp. 515-519 (2009).

(56) References Cited

OTHER PUBLICATIONS

Strukov et al., "Resistive Switching Phenomena in Thin Films: Materials, Devices, and Applications," MRS Bulletin, vol. 37, pp. 108-114 (2012).
Valov et al., "Nanobatteries in Redox-Based Resistive Switches Require Extension of Memristor Theory," (2013).
Wise et al., "Microelectrodes, Microelectronics, and Implantable Neural Microsystems," Proceedings of the IEEE, vol. 96, No. 7, pp. 1184-1202 (Jul. 2008).
Xing et al., "An FPGA-Based Instrument for En-Masse RRAM Characterisation with ns Pulsing Resolution," IEEE Transactions on Circuits and Systems (2015).
Yang et al., "Memristive Devices for Computing," Nature Nanotechnology, vol. 8, pp. 13-24 (2013).
Yu et al., "An Electronic Synapse Device Based on Metal Oxide Resistive Switching Memory for Neuromorphic Computation," IEEE Transactions on Electron Devices, vol. 58, No. 8, pp. 2729-2737 (Aug. 2011).
Zeck et al., "Axonal Transmission in the Retina Introduces a Small Dispersion of Relative Timing in the Ganglion Cell Population Response," PLoS One, vol. 6, Issue 6, e20810 (Jun. 2011).
Zeitler et al., "Extracellular Voltage Noise Probes the Interface Between Retina and Silicon Chip," Applied Physics Letters, 99, 263702 (2011).

\* cited by examiner

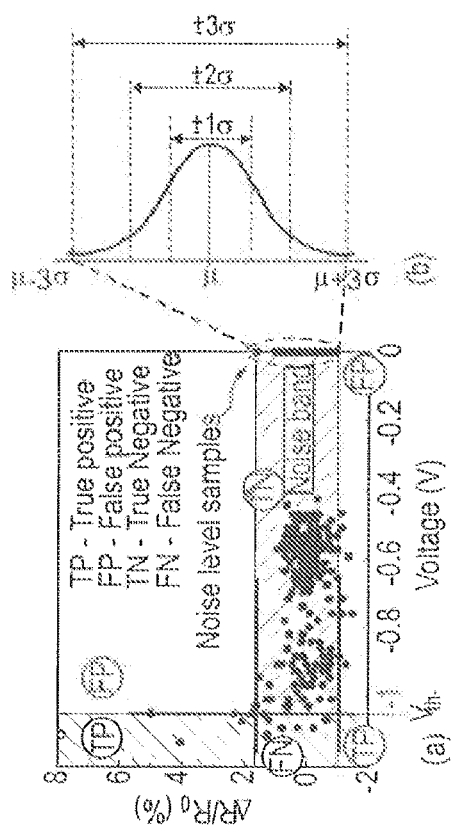
Fig. 12
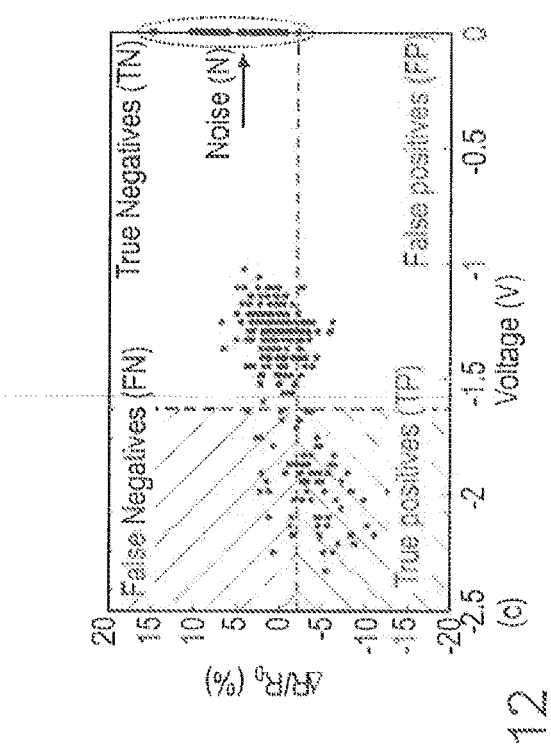
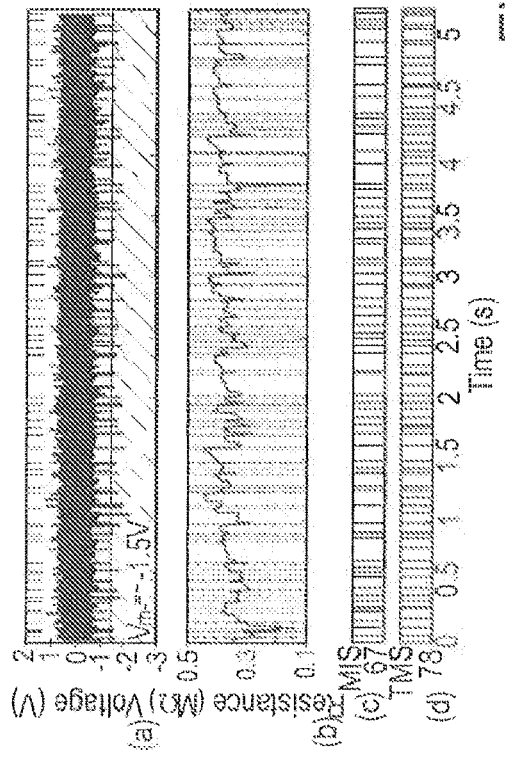
Fig. 13
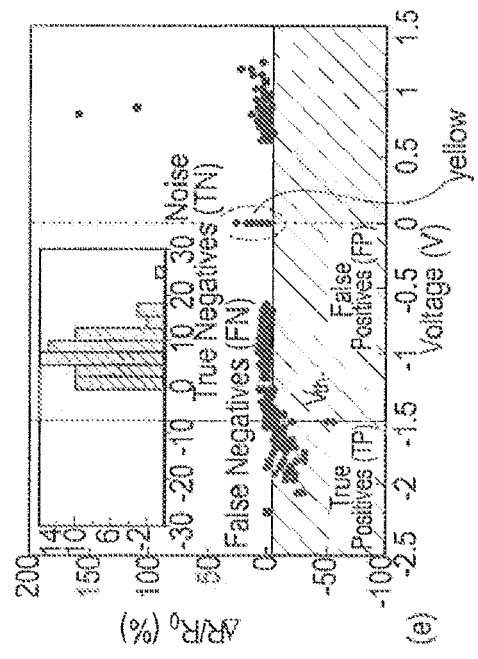

Fig. 18
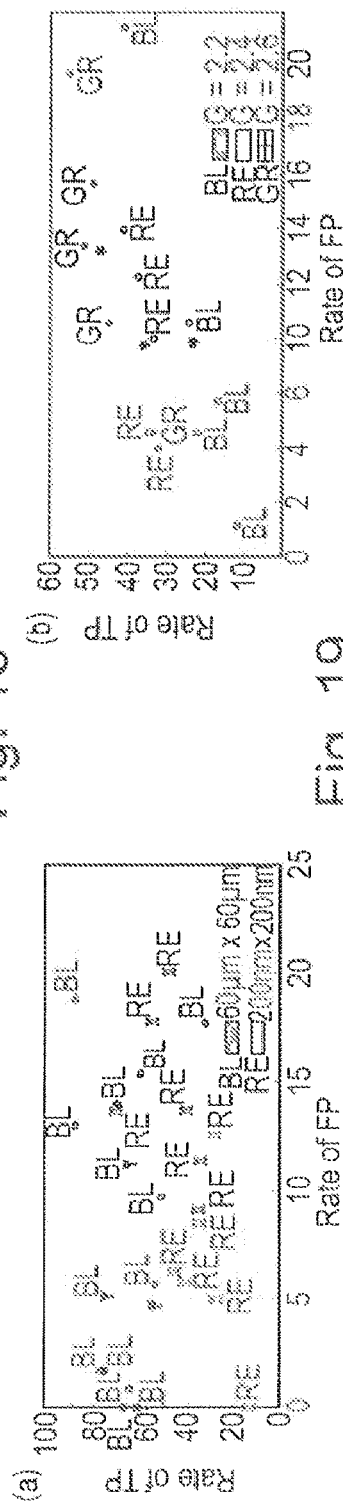
Fig. 19
Fig. 20
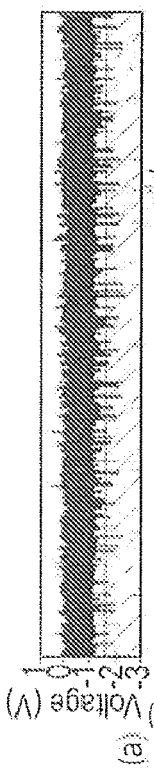
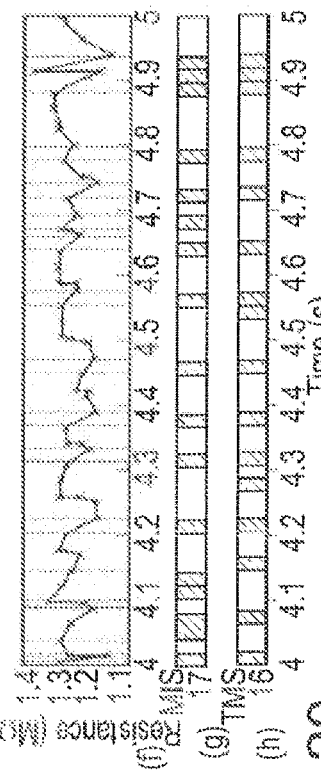

Table 1

| Device Dimensions | Vis-(V) | Gain | Offset | MIS | TMS | TP | FP | TN | FN | Rate of TP (%) | Rate of FP (%) |
|---|---|---|---|---|---|---|---|---|---|---|---|
| 60x60 μm² | -1.4 | 3.2 | 0 | 67 | 78 | 58 | 9 | 166 | 20 | 74.35 | 5.14 |
| 60x60 μm² | -1.4 | 2.6 | 0 | 39 | 20 | 13 | 26 | 207 | 7 | 65 | 11.15 |
| 60x60 μm² | -1.17 | 2.4 | -0.6 | 22 | 20 | 11 | 11 | 222 | 9 | 55 | 4.7 |
| 60x60 μm² | -1.7 | 2.4 | -0.4 | 15 | 20 | 13 | 2 | 231 | 7 | 65 | 0.85 |
| 60x60 μm² | -1.1 | 2 | 0 | 15 | 20 | 13 | 2 | 231 | 7 | 65 | 0.85 |
| 60x60 μm² | -0.7 | 2.2 | 0 | 74 | 78 | 47 | 27 | 148 | 31 | 60.26 | 15.4 |
| 60x60 μm² | -0.7 | 2.2 | -0.2 | 52 | 78 | 42 | 10 | 165 | 36 | 53.8 | 5.71 |
| 60x60 μm² | -1.34 | 2.2 | 0 | 12 | 20 | 12 | 0 | 233 | 8 | 60 | 0 |
| 60x60 μm² | -1 | 4.4 | 0 | 56 | 78 | 25 | 31 | 144 | 53 | 32 | 17.7 |
| 60x60 μm² | -1 | 4.4 | 0 | 57 | 78 | 40 | 17 | 158 | 38 | 51.3 | 9.7 |
| 60x60 μm² | -1 | 4.8 | 0 | 76 | 78 | 53 | 23 | 152 | 25 | 70 | 14 |
| 60x60 μm² | -1.2 | 4.8 | -0.2 | 102 | 78 | 69 | 33 | 142 | 9 | 88.46 | 18.8 |
| 60x60 μm² | -1.2 | 2.9 | 0 | 62 | 78 | 59 | 3 | 172 | 19 | 75.6 | 1.71 |
| 60x60 μm² | -1.2 | 2.6 | 0 | 63 | 78 | 60 | 3 | 172 | 18 | 77 | 1.71 |
| 60x60 μm² | -2.43 | 4.4 | 0 | 13 | 20 | 13 | 0 | 233 | 7 | 65 | 0 |
| 60x60 μm² | -0.7 | 2.6 | -0.4 | 92 | 78 | 69 | 23 | 152 | 9 | 88.4 | 13 |
| 200x200 nm² | -1.1 | 2.8 | -0.4 | 54 | 78 | 31 | 24 | 151 | 47 | 40 | 13.7 |
| 200x200 nm² | -1.25 | 2.6 | -0.6 | 46 | 78 | 35 | 11 | 164 | 43 | 44.8 | 6.28 |
| 200x200 nm² | -1.3 | 2.6 | -0.6 | 30 | 78 | 21 | 8 | 166 | 57 | 27 | 5 |
| 200x200 nm² | -1.63 | 2.8 | -0.4 | 18 | 78 | 10 | 0 | 175 | 68 | 12.8 | 0 |
| 200x200 nm² | -1.25 | 2.6 | -0.6 | 42 | 78 | 32 | 10 | 165 | 46 | 41 | 5.74 |
| 200x200 nm² | -1.25 | 2.6 | -0.6 | 78 | 78 | 54 | 24 | 151 | 24 | 70 | 13.7 |
| 200x200 nm² | -1.3 | Max=3 | Min=-2.2 | 44 | 78 | 22 | 22 | 153 | 56 | 28.2 | 12.8 |
| 200x200 nm² | -1.13 | 2.6 | -0.6 | 47 | 78 | 27 | 20 | 155 | 51 | 34.6 | 11.4 |
| 200x200 nm² | -1.2 | 3 | -0.6 | 47 | 78 | 27 | 20 | 155 | 51 | 34.6 | 11.4 |
| 200x200 nm² | -1.3 | 3 | -0.6 | 42 | 78 | 27 | 15 | 160 | 51 | 34.6 | 8.5 |
| 200x200 nm² | -1.3 | 2.6 | -0.6 | 74 | 78 | 43 | 31 | 144 | 35 | 55.12 | 17.71 |
| 200x200 nm² | -1.4 | 2.6 | -0.6 | 72 | 78 | 37 | 35 | 140 | 41 | 47.43 | 20 |
| 200x200 nm² | -1.45 | 2.6 | -0.6 | 43 | 78 | 27 | 16 | 159 | 51 | 34.61 | 9.14 |

Fig. 21

Table 2

| Device Dimensions | Gain | Offset | MJS | FMS | TP | FP | TN | FN | Rate of TP (%) | Rate of FP (%) |
|---|---|---|---|---|---|---|---|---|---|---|
| 200x200 nm² | 2.2 | -0.6 | 66 | 78 | 32 | 34 | 141 | 46 | 41.02 | 19.42 |
| 200x200 nm² | 2.2 | -0.6 | 25 | 78 | 17 | 8 | 167 | 61 | 21.79 | 4.57 |
| 200x200 nm² | 2.2 | -0.6 | 23 | 78 | 13 | 10 | 165 | 65 | 16.67 | 5.71 |
| 200x200 nm² | 2.3 | -0.6 | 34 | 78 | 19 | 15 | 160 | 59 | 24.35 | 8.57 |
| 200x200 nm² | 2.3 | -0.6 | 11 | 78 | 9 | 2 | 173 | 69 | 11.53 | 1.14 |
|  |  |  |  |  |  |  |  |  | 23.07 | 7.88 |
| 200x200 nm² | 2.4 | -0.6 | 32 | 78 | 25 | 7 | 168 | 53 | 32.05 | 4 |
| 200x200 nm² | 2.4 | -0.6 | 47 | 78 | 29 | 18 | 157 | 49 | 37.18 | 10.28 |
| 200x200 nm² | 2.4 | -0.6 | 40 | 78 | 26 | 14 | 161 | 52 | 33.34 | 8 |
| 200x200 nm² | 2.4 | -0.6 | 53 | 78 | 32 | 21 | 154 | 46 | 41.02 | 12 |
| 200x200 nm² | 2.4 | -0.6 | 35 | 78 | 27 | 8 | 167 | 51 | 34.61 | 4.57 |
|  |  |  |  |  |  |  |  |  | 35.64 | 7.77 |
| 200x200 nm² | 2.6 | -0.6 | 62 | 78 | 38 | 24 | 151 | 40 | 48.71 | 13.71 |
| 200x200 um² | 2.6 | -0.6 | 50 | 78 | 35 | 15 | 160 | 43 | 44.87 | 8.57 |
| 200x200 nm² | 2.6 | -0.6 | 60 | 78 | 40 | 20 | 155 | 38 | 51.28 | 11.42 |
| 200x200 nm² | 2.6 | -0.6 | 34 | 78 | 26 | 8 | 167 | 52 | 33.34 | 4.57 |
| 200x200 nm² | 2.6 | -0.6 | 74 | 78 | 43 | 31 | 144 | 35 | 55.128 | 17.71 |
|  |  |  |  |  |  |  |  |  | 46.66 | 11.19 |

Fig. 22

METHOD AND SYSTEM FOR DETECTING EVENTS IN AN INPUT SIGNAL USING VOLATILE MEMRISTOR STATE CHANGE

CROSS REFERENCE TO RELATED APPLICATIONS

This application is a National Stage Entry of PCT/GB2017/053119 filed Oct. 16, 2017, which claims benefit to GB Application 1619154.6 filed Nov. 11, 2016, which are incorporated by reference as if fully set forth.

FIELD OF INVENTION

The present invention relates to detecting events in an input signal. Particularly in the context of detecting events in a neurological input signal.

BACKGROUND

Advanced neural interfaces mediating bio-signals between brain and various technological devices bear great potential for future technologies aiming at restoring and enhancing organ functions. The progress in neural recording techniques has allowed an exponential growth in the number of simultaneously recorded neurons leading to creation of big neural data. A key bottleneck in advancement of efficient bio-electronic links is to implement on-node neural processing of recorded neural signals at low computational cost which further imposes additional constraints on bandwidth, energy and also the silicon-area.

Reverse engineering the human brain and decoding the information processes underlying the biological processes requires integrated efforts from researchers with different scientific backgrounds[1]. Over the past decade advances in neural recording techniques[2,3,4,5,6] have led to enormous progress in acquiring electrophysiological data from multi-unit cells in-vitro or in-vivo contributing towards the understanding of neuroscience. The state-of-the-art implementations presently can record from up to thousand sites in parallel in-vivo[7] and from up to 30 k[8] sites in-vitro using Complementary Metal Oxide Semiconductor (CMOS) based High Density Microelectrode Arrays (HDMEA's). Simultaneously, there has been considerable progress in neural processing microsystems[9,10] which are capable of detecting neural spiking activity on-node[11,12]. The relevant spike-detected information can then be transmitted off-line wirelessly and techniques such as a Template Matching System (TMS) or a Principle Component Analysis (PCA)[13] can be used off-line for spike-sorting[14]. These techniques consist of mapping the recorded neural activity to the source active neurons offering insights in neural coding principles[15] and thus bear great potential for neuroprosthetic applications[16,17,18,19] Further advances in the fast developing field of implantable neural interfaces[20] are obstructed by key bottlenecks such as: a) computational power required to process ever increasing, huge volume of neural signals (Gb/s range presently) on-node in real-time[21,22,23]; b) bandwidth[24]; c) scalability (as the large signal-processing circuitry may not be suitable for implantable purposes; and d) most importantly, the amount of power dissipated per channel[25]. Therefore, intelligent solutions capable of addressing the identified bottlenecks are urgently needed.

Recently, a neural spike-detector based on emerging solid-state, two terminal metal-oxide devices commonly known as memristor[26,27,28] has been proposed[29]. A memristor may otherwise be referred to as a device or resistive switching component. Fundamentally, memristor-based devices are capable of undergoing non-volatile resistive state transitions as a function of integral of input voltage and thus behave as threshold input integrators[30]. In the past decade, memristive devices have been researched for applications such as non-volatile memories[31] and neuro-inspired computing[32,33,34], however, previous work has shown the use of $TiO_x$-based memristive devices for spike-detection for the first time.

Pre-recorded extracellular neural waveforms obtained from retinal ganglion cells using CMOS-based Multi-Electrode Array (MEA)[35,36,37] were used to bias the memristor devices (i.e. resistive switching components). The significant supra-threshold events (spikes) were encoded in gradual, non-volatile resistive state transitions[38] of a device-under-test (DUT), wherein the device-under-test is a specific resistive switching component being tested, whereas the sub-threshold events (i.e. noise) were naturally filtered-off. This property makes these devices suitable as noise-suppressing integrating sensors and are thus termed as 'Memristive Integrating Sensors (MIS)', which is another name for a resistive switching device, A limiting factor impeding the detection performance of the proposed integrating sensor was the saturation of the resistive state of the resistive switching component being tested (the DUT) wherein the resistive switching components failed to register any significant activity in the neural waveform post-saturation[39,40]. Consequently, the performance of the resistive switching components (i.e. the devices) was optimised by introducing manual frequent resets in the initial resistive state of the resistive switching component (i.e. the device). Resetting of the device using a single pulse upon saturation doubled the detection accuracy of the MIS platform[39].

SUMMARY

It is an object of the present invention to provide a way of detecting events in an input signal.

According to an aspect of the invention, there is provided a method for detecting events in an input signal comprising: applying an output from at least one sensor to a resistive switching component, wherein the resistive switching component is configured to undergo a volatile resistive state change from an initial resistive state to a further resistive state when a voltage with a magnitude less than or equal to an upper threshold value is applied across the resistive switching component, and the volatile resistive state change is such that the resistive switching component spontaneously relaxes from the further resistive state towards or beyond the initial resistive state after the magnitude of the voltage subsequently falls; sampling a further signal that is dependent on a resistance of the resistive switching component; and identifying, using the sampled further signal, a sequence of volatile resistive state changes corresponding to events in the input signal.

According to another aspect of the invention, there is provided a system for detecting events in a signal, comprising: a resistive switching component configured to undergo a volatile resistive state change from an initial resistive state to a further resistive state when a voltage with a magnitude less than or equal to an upper threshold value is applied across the resistive switching component, and the volatile resistive state change is such that the resistive switching component spontaneously relaxes from the further resistive state towards or beyond the initial resistive state after the magnitude of the voltage subsequently falls; and a processing unit configured to sample a further signal that is dependent on a resistance of the resistive switching component and identify, using the sampled further signal, a sequence of volatile resistive state changes corresponding to events in the input signal.

BRIEF DESCRIPTION OF THE DRAWINGS

The invention will be more clearly understood from the following description, given by way of example only, with reference to the accompanying drawings, in which:

FIGS. 12a and b depict a comparison of the noise band diagrams in volatile and non-volatile regions of operation;

FIGS. 13a-e depict spike-detection of the MIS system in the volatile region and benchmarking of the results against a Template Matching System (TMS);

FIG. 18 depicts spikes detected by the Template Matching system;

FIGS. 19a and b depict a comparison of Receiver Operating Characteristics (ROC) that is a rate of true positives vs rate of false positives for memristors of micro and nano dimensions; and FIGS. 20a-h relate to Scalability of exemplary $TiO_x$ devices to the nanoscale dimensions and operation of nano-devices as MIS elements.

FIGS. 21 and 22 depict Tables 1 and 2.

DETAILED DESCRIPTION OF THE PREFERRED EMBODIMENT(S)

Figure 1:
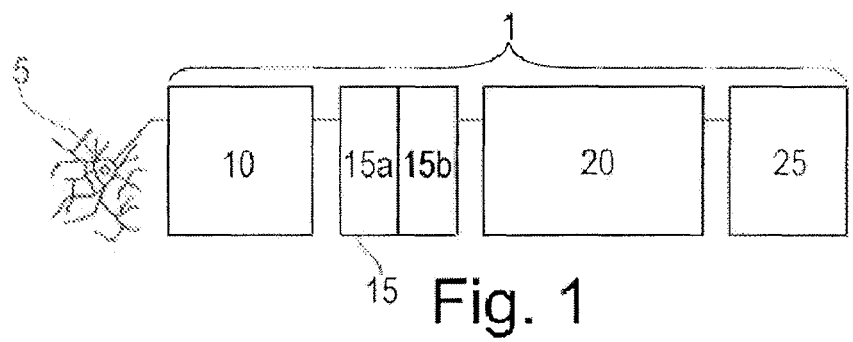
FIG. 1 depicts a system for processing data from an event in accordance with an embodiment.

The same references are used for similar features throughout the drawings. The features shown in the figures are not necessarily to scale and the size or arrangements depicted are not limiting. It will be understood that the figures may include optional features which are not essential to any embodiments. Furthermore, not all of the features are depicted in each figure and the figures may only show a few of the components relevant for a describing a particular feature.

As described below, a new concept is presented where the inherent volatile properties of resistive switching components, e.g. nano-scale memristive devices, can be used to compress information on neural spikes in real-time. In principle, the intrinsic voltage-threshold of the resistive switching components (e.g. the metal-oxide devices) can be used to differentiate the spiking activity from the background activity. It will be described that the information on spike amplitude and frequency of the neural signals recorded using a multi-electrode array can be transduced in the metastable resistive state transitions of a single resistive switching component, such as a nano-scale device, inherently capable of self-resetting and thus continuously detecting spiking activity. The operation of resistive switching components (i.e. devices) can be in a very high resistive state range which can reduce the power dissipated per channel to less than 100 nW. This demonstrates the potential of the method and system according to an embodiment to build scalable, yet energy-efficient on-node processors for advanced brain-chip interfaces.

In an embodiment, a method is provided for detecting events in an input signal. The method may comprise applying an output from at least one sensor to a resistive switching component. The resistive switching component may be configured to undergo a volatile resistive state change from an initial resistive state to a further resistive state when a voltage with a magnitude ales than or equal to an upper threshold value is applied across the resistive switching component. Additionally, the volatile resistive state change of the resistive switching component may be such that the resistive switching component spontaneously relaxes from the further resistive state towards or beyond the initial resistive state after the magnitude of the voltage subsequently falls. In other words, when a voltage of a magnitude less than or equal to the upper threshold value is applied to the resistive switching component, the resistive switching component may change resistive state and immediately, spontaneously return to a different state, possibly similar to a resistive state before such a voltage was applied, as soon as the voltage is removed. The voltage subsequently falling may mean that the voltage reaches a peak, and as soon as the voltage reduces below the peak magnitude, the resistive switching component 20 may respond with a change in resistive state. The subsequent falling of the voltage may be immediate following a rapid rise in the voltage. The magnitude of the voltage may rapidly increase and reduce and may be considered as a spike in the voltage applied to the resistive switching component 20.

The initial resistive state is the resistive state of the resistance switching component before an event resulting in a resistive state change occurs. The initial resistive state may change as described in further detail below. Thus, over time, the resistive state may be considered as the initial resistive state on multiple occasions, i.e. just before a state change. The further resistive state is a resistive state which is different to the initial resistive state. The further resistive state is the resistive state induced by the voltage applied to the resistive switching component. The further resistive state may only be reached instantaneously, i.e. the further resistive state may be reached temporarily and immediately the resistive state may change towards or beyond the initial resistive state.

After the voltage falls, the resistive state may return towards or beyond the initial resistive state. In other words, when the magnitude of the voltage starts to decrease, the resistive state of the resistive switching component may start to immediately change, and the change is a relaxation away from the further resistive state. The relaxation is towards or beyond the initial resistive state such that the resistive state may return to the same value as initial resistive state, or may have a magnitude which is larger or smaller than the initial resistive state.

In an example, when the voltage below the upper threshold value is applied, the resistive state of the resistive switching component changes from the initial resistive state and the magnitude of the resistive state may decrease to a different resistive state which is considered to be a further resistive state. In this example, when the voltage subsequently falls, the magnitude of the resistive state increases (i.e. towards the initial resistive state) and thus the resistive state relaxes. In an alternative example, when the voltage below the upper threshold value is applied, the resistive state of the resistive switching component changes from the initial resistive state and the magnitude of the resistive state may increase to a different resistive state which is considered to be a further resistive state. In this example, when the voltage subsequently falls, the magnitude of the resistive state decreases (i.e. towards the initial resistive state) and thus relaxes. In either case, it is not necessary for the resistive state to relax fully to, or beyond, the initial resistive state, however, this may occur.

The method may further comprise sampling a further signal that is dependent on a resistance of the resistive switching component. The method further comprises identifying, using the sampled further signal, a sequence of volatile resistive state changes corresponding to events in the signal.

One of the major advantages of the method of the embodiment (i.e. the proposed disruptive spike-detecting approach) lie in its high potential for scalability and low power dissipation. These features are extremely beneficial and may even be indispensable requirements for the next-generation of implantable neural interfaces. These embodiment exploit an often overlooked crucial property of a resistive switching component (otherwise known as a memristive device), that is 'volatility'[41,42,43,44]. Furthermore, the method of the embodiment demonstrates a new concept for optimised event detection in a signal, such as neural spike-detection, using this property. In a volatile region, the resistive switching component may exhibit metastable memory state transitions following which the resistive state spontaneously relaxes from the further resistive state towards or beyond the initial resistive state For example, the initial resistive state may be considered to be an equilibrium resistive state and the resistive switching component may inherently relax to an equilibrium resistive state in a definite time window. It will be described in further detail below that this volatility property naturally reduces, or optimally eliminates, the need for manual resets needed in non-volatile resistive switching devices, in order to overcome saturation thus saving on the power budget. Additionally, because the resistive switching component spontaneously relaxes, it does not saturate in the same way as a non-volatile resistive switching component might and thus, using a volatile resistive switching component has improved sensitivity over time. Additionally, an experiment will be described which shows that the resistive switching component (i.e. the memristive device) can be operated in much higher resistive state regions than non-volatile resistive switching components. Operating in such a higher resistive state region can cut the power dissipated to less than 100 nW, much lower than the current state-of-the-art spike detectors (which is 800 nW approximately)[25]. Lastly, exemplary $TiO_x$ based resistive switching components (otherwise referred to as MIS elements) can be scaled down from micro- to nano-scale devices, and exemplary 200 nm×200 nm devices are employed to illustrate the effects of size on resistive switching component (MIS) performance. Although $TiO_x$ devices are described, it will be understood that other materials may be used as well or instead, for example, tungsten oxide may be used instead.

The event may be any type of event which relates to a waveform of an appropriate form. Thus, if the waveform is a voltage/current series over time, then events may be indicated by a change in the waveform which can be detected by a sensor. The input signal may be a biological signal. The event may be a biological event. Preferably, the input signal may be a neurological signal. Preferably, the event may be a neurological event. An example of a neurological event may be a firing of a neuron. The spike in a neural waveform during a neurological event may be caused by an action potential being generated by a neuron, which results in a sharp deviation from the baseline of the neural waveform. The input signal is the signal which is input to a sensor. The waveform (e.g. the neural waveform) may be represented by, or otherwise considered to be the same as, the input signal. Thus, events in the input signal are considered to be the same as, or at the very least indicative of, events in the waveform. The input signal may be generated by sampling whatever is being tested, for example a neuron.

An exemplary system 1 for carrying out the method is depicted in FIG. 1. As shown, a sensor 10 may be used to take measurements, for example, of a neuron 5. Thus, for example, the sensor 10 may measure a neural waveform at a particular location. The sensor 10 may pick up variations due to multiple neurons. The neural waveform thus indicates neurological events by spikes in the neural waveform relating to multiple neurons. The sensor 10 receives the neural waveform as an input signal and outputs an electrical output. The output may be sent to an optional voltage modifying device 15 to boost the voltage of the output from the neurological sensor 10. The output has a variation of voltage over time. A resistive switching component 20 may be provided which undergoes changes in resistive state in response to the voltage of the output applied across it. A processing unit 25 may be provided for sampling a further signal and identifying a sequence of volatile resistive state changes corresponding to events in the input signal. For further details of a resistive switching component, please see "Real-time encoding and compression of neuronal spikes by metal-oxide memristors" by Isha Gupta, Alexantrou Serb, Ali Khiat, Ralk Zeitler, Stefano Vassanelli and Themistoklis Prodromakis, Nature Communications (ncomms12805).

The sensor 10 may be any sensor capable of detecting waveforms described above and capable of detecting events in the waveform, i.e. in the input signal. For example, if the input signal being detected relates to a biological signal, the sensor 10 may be a biological sensor, or more particularly, if the input signal being detected relates to a neurological signal, the sensor 10 may be a neurological sensor. In other words, the type of sensor will depend on the type of waveform being detected.

The sensor 10 may be configured and used, as depicted in FIG. 1, to detect events in a signal. The sensor 10 may be used in various ways, for example, in vitro or in vivo. The sensor 10 may store measurements at the sensor 10. Alternatively, the measurements may be passed in real time (or with minor delay) to the resistive switching component 20 or may be stored in another device which can send the measurements to the resistive switching component 20 at a desired time.

The output from the sensor 10 is normally an electrical output which has a voltage. The voltage of the output varies over time. The voltage of the output varies depending on the input signal, e.g. the neural waveform, and spikes in the input signal lead to corresponding spikes in the voltage of the output. Thus there are large, sharp increases in the voltage of the output when an event occurs.

When the voltage is applied across the resistive switching component 20, the resistance of the resistive switching component 20 changes. Thus, the resistance of the resistive switching component 20 may result from applying the output from at least one sensor 10 across the resistive switching component 20. The resistance of the resistive switching component 20 varies over time due to the varying input voltage (of the output of the sensor 10 which may optionally have passed through a voltage modifying device 15). The output of the sensor 10 may be considered as the input to the resistive switching component 20.

As will be described in further detail below, the resistive switching component 20 may undergo a resistive state change when a voltage below or the same as the upper threshold value is applied across it. A resistive state change is indicated by a sharp change in the resistance of the resistive switching component 20. Large changes in resistance may correspond to resistive state changes.

A sequence of resistive state changes may occur as a result of the voltage variation applied to the resistive switching component 20 over time. A resistive state change may comprise a change in resistance at a constant temperature, or a substantially constant temperature. A change in resistance does not necessarily equate to a change in resistive state, however, a resistive state change does include a change in resistance. Small variations in the input signal would not likely lead to a change in the output from the sensor 10 which would alter the resistive state of the resistive switching component 20. However, changes that are large enough will lead to resistive state changes.

The resistive switching component 20 may otherwise be referred to as a memristor or memristor device. The dominant device behavioural feature of the resistive switching component 20 may be the memristance of the component, i.e. the ability of the resistive switching component 20 to retain, even for a very short time, the variation of resistance of the component. Various devices may be considered as a resistive switching component 20. For example, RRAM, FeRAM, STTRAM, PCMRAM and others are different forms or technological implementations of components exhibiting resistive switching. For convenience, these devices may be referred to as memristors, or resistive switching components.

When the voltage is of a magnitude less than or equal to the upper threshold, a volatile resistive state change of the resistive switching component 20 occurs. The volatile resistive state change is such that the resistive switching component 20 spontaneously relaxes from the further resistive state towards or beyond the initial resistive state after the magnitude of the voltage subsequently falls. This means that an event (e.g. a spike) in the output from the sensor 10 results in a corresponding spike in the resistance of the resistive switching component 20 which may correlate to a resistive state change.

As soon as the event is over and the voltage decreases, the resistance of the resistive switching component 20 increases, and the resistive state of the resistive switching component 20 relaxes. The resistive switching component 20 is changed to a resistive state by an event, and the reduction of the voltage means that the resistive state returns to a different state than the resistive state reached during the event. The resistive switching component 20 spontaneously relaxing means that further input is not required to change the resistive state, it will simply respond to the removal of the increased voltage in the input signal. In other words, it will automatically return towards or beyond the initial resistive state from before the event. In other words, the resistive state relaxes from its immediately post-stimulus value towards an equilibrium level, which may be close to its pre-stimulus value, i.e. the initial resistive state, though this is not necessary. Thus, the resistive switching component 20 can relax back to a similar resistive state as the initial resistive state before the event (i.e. a different resistive state to the one reached during the application of the voltage which caused the resistive state change). The resistive state changes may be negative, which means that the resistance of the resistive switching component 20 may relax to a higher value after an event has occurred. The resistive state may take longer to relax toward a previous resistive state if there are several events in quick succession.

It has been previously described that non-volatile resistive switching components are also known, in which the resistive state change is retained, possibly indefinitely. Thus, the resistive switching component having a volatile resistive state change may otherwise be referred to as a volatile resistive switching component due to the spontaneous relaxation of the resistive state. The resistive state change may only be volatile if the applied voltage is less than or equal to the upper threshold value. In other words, the resistive switching component 20 may be operated in a volatile regime when the voltage has a magnitude less than or equal to the upper threshold value.

However, if the voltage increases above the upper threshold value, the resistive switching component 20 may not have a volatile response. Instead, when the voltage due to a particular event is greater than the upper threshold value, the resistive state may not relax spontaneously immediately after the voltage relating to that particular event is removed. Thus, there may be a more permanent change in the resistive state, which means that the resistive switching component 20 can have non-volatile responses in addition to the volatile responses. Thus, the upper threshold value may otherwise be referred to as the non-volatile threshold value. This may be due to a number of events occurring in quick succession, i.e. the voltage having a magnitude which has spikes with rapidly increasing magnitudes repeatedly in a short time period, or due to the voltage increasing above the magnitude of the upper threshold value at least once. However, as described below, it may be preferable to operate the resistive switching component 20 solely, or at least mostly, in the volatile regime (i.e. with voltages having magnitudes less than or equal to the upper threshold value) to avoid the resistive switching component becoming saturated. The majority of the resistive changes will still be volatile, thus permanent (or even semi-permanent) increases in the resistive state are not expected often. Thus, it is unlikely that saturation will occur, and if it does, it will occur significantly less often than for the same signals being applied to non-volatile resistive switching components.

As described, the resistive switching component may operate in the volatile regime such that volatile resistive state changes occur in which the resistive state relaxes after an event. It is noted that in addition to the volatile responses, the resistive switching component 20 may also have a non-volatile resistive state change. This may be in addition to the volatile resistive state changes. Thus, the resistive switching component may be configured to undergo a non-volatile resistive state change when a voltage with a magnitude above the magnitude of the upper threshold value is applied to the resistive switching component, wherein the non-volatile resistive state change is such that the resistive switching component does not spontaneously relax from the further resistive state towards or beyond the initial resistive state after the magnitude of the voltage subsequently falls. In other words, after a non-volatile state change, the resistive state may remain at the further resistive state (at least until another event occurs).

The non-volatile resistive state change may last for significantly longer than the relatively instantaneous volatile resistive state change. The non-volatile resistive state change may last for at least an hour, or possibly more. The non-volatile resistive state change may be retained for multiple hours, days, months or even years. It is noted that the existence of a non-volatile resistive state change does not preclude coexistence with a volatile resistive state change. For example, the resistive switching component 20 may have volatile resistive state changes after non-volatile resistive state changes occur. However, the non-volatile resistive state change may result in a more long term change which may mean that the volatile resistive state changes relates to a different range of values than before the non-volatile resistive state change. In other words, if the non-volatile resistive state changes can be considered to have a range of resistive states which are considered to be an equilibrium level, the non-volatile resistive state change may alter the range of values of the equilibrium level, for example increasing (or decreasing) the magnitude of the equilibrium resistive state. This change will be long term and mean that the resistive switching component 20 relaxes to state changes different than the state changes before the non-volatile resistive state change.

Optionally, the resistive switching component 20 may also have a lower threshold value. The resistive switching component 20 may be configured to undergo a volatile resistive state change when a voltage with a magnitude greater than or equal to the lower threshold value is applied across the resistive switching component 20. Thus, the resistive switching component 20 may undergo a volatile resistive state change from an initial resistive state to a further resistive state when a voltage with a magnitude less than or equal to the upper threshold value is applied across the resistive switching component 20. More generally, the resistance of the resistive switching component 20 may not change enough to cause a resistive state change when the voltage has a magnitude below the lower threshold value. The output comprises spikes in the voltage which may correlate to an event. However, the voltage of the output may need to be large enough to register a change in the resistance of the resistive switching component 20.

The lower threshold value may otherwise be referred to as the intrinsic switching threshold and/or the volatile threshold value. The lower threshold value is the voltage below which the output may not change the resistive state of the resistive switching component. Thus, the resistive switching component 20 optionally comprising a lower threshold as described may therefore be considered to be noise suppressing because it may not register a change when the voltage applied across the resistive switching component 20 is below the lower threshold value. In other words, the volatile resistive switching component may have inherent noise filtering. If the voltage is below the lower threshold value, then the resistive state of the resistive switching component 20 will not necessarily be changed, meaning that the resistive switching component 20 may not adequately respond to the output from the sensor 10. Thus, there may not be a resistive change unless the voltage is greater than or equal to the lower threshold value.

The method comprises sampling a further signal that is dependent on a resistance of the resistive switching component 20. The sampling may be carried out by a processing unit 25. In other words, the method comprises sampling a signal based on the output of the resistive switching component. This may correspond directly to the resistance of the resistive switching component 20 or may be a transformed version of the resistance of the resistor switching component 20. Possible transformation of the output of the resistive switching component 20 is described in further detail below. The sampling can be carried out in different ways and comprises measuring and recording a value of the further signal at a specific point in time.

Optionally, the sampling is carried out periodically. For example, the sampling may be carried out at equal time intervals. Preferably, the sampling is carried out at frequency greater than or equal to approximately 30 Hz. More preferably, the frequency is greater than or equal to approximately 50 Hz. It will be understood that different input signals may require different sampling frequencies in order to sample the further signal adequately often to obtain the desired information from the further signal. Sampling periodically may mean that sampling is carried out more often than using a different sampling technique, but it does not require monitoring of the further signal which may use up power.

A more detailed example of how the frequency of sampling the further signal may be determined is provided. In an example, the input signal may comprise approximately 64,000 samples, lasting approximately 5.2 s. The output from the sensor may be received by the resistive switching component 20 in batches, wherein each batch is a 1000 sample points for example. In a batch of 1000 points, the resistive state of the resistive switching component may be read after every 300 points i.e. at 300, 600, 900 and then at 1000. An additional measurement may optionally be taken at the end of each batch (for estimating the reference/noise values as it can be seen in DeltaR/V plots). Therefore, one batch contains 5 reads, and it follows that 64 batches are approximately equal to 320 reads. Thus, if 320 samples of the further signal are taken in 5.2 seconds, this means that a sample of the further signal is taken approximately every 0.02 seconds. Hence, the frequency of sampling the further signal may be low, i.e. approximately 50 Hz.

Alternatively, the sampling may be carried out in a different way. For example, the sampling may be synchronised with the occurrence of an event. In other words, the sampling may comprise monitoring and outputting when a portion of the further signal meets certain condition. For example, the method may comprise monitoring the resistance of the resistor switching component 20 and specifically sampling the further signal when a resistive state change (corresponding to an event in the signal) occurs. This may be detected for example by a change in the resistance which is greater than the predetermined value, or a rate of change of the resistance which is greater than another predetermined value. Thus, the certain conditions may be the value of the predefined change or the rate of change in a predefined time. The monitoring may be carried out constantly. The monitoring may be passive (i.e. not require active sampling unless a further step is carried out). Monitoring the further signal in this way may comprise similar steps to the step of identifying a volatile resistive state change as described below. Detecting a change which is greater than a predetermined value may be considered as a tripwire type mechanism. Sampling in a synchronized way as described does require the use of power to monitor the further signal, however, as the further signal will only be sampled when it appears that an event has occurred, the amount of power may be reduced and/or optimized, by avoiding unnecessary sampling as may be the case when sampling periodically.

The method may comprise a step of identifying the events based on sampling the further signal the resistive switching component 20. In further detail, the step may include identifying a volatile resistive state change corresponding to an event. The identifying step may optionally be carried out by the processing unit 25. The identifying step may compare portions of the further signal. The identifying step may comprise identifying a change in the further signal relative to a portion of the further signal detected after a preceding event. The identifying step may further comprise determining that the change in the further signal is greater than a predetermined value. In other words, that the change in the further signal since the last event is greater than a predetermined value. The change in resistance being above a predetermined value indicates that a resistive state change may have occurred. The step of identifying may be based on the magnitude of the change in the further signal and/or the rate of change of the magnitude of the further signal in a predefined time interval. When the change or rate of change is greater than a predetermined value, it indicates a correlation to the event because the resulting spike in the input signal would likely be large enough to cause a spike in the voltage of the output which, when applied to the resistive switching component 20, would result in the detected change.

The predefined value of change can be set, for example, based on previous analysis of data values relating to relevant types of events. Similarly, the predefined time interval can also be set, for example, based on previous analysis of data values relating to neurological events. In this way variation of the further signal can be identified as relating to a spike (i.e. an event, or more particularly a neurological event). This means that variation in the waveform which does not result in a significant enough change in the further signal would not result in a resistive state change. The method may only process the further signal which possibly relate to events (i.e. the changes or rates of change which are large enough) meaning that other variations in the further signal may be considered (and optionally ignored) as noise.

The resistive switching component 20 may be configured to operate in a wide range of resistances. The range of resistances will depend on the specific resistive switching component 20 which is used. Thus, for example, the resistive switching component 20 may be configured to operate in a range of resistances from approximately 0.1 MΩ approximately 3 MΩ, or more preferably from approximately 0.7 MΩ approximately 1.4 MΩ. It will be understood that these ranges are exemplary. The resistive switching component 20 may be configured to operate in a resistance higher than approximately 0.1 MΩ, or preferably higher then approximately 0.7 MΩ. Additionally or alternatively, the resistive switching component 20 may be configured to operate at a resistance of less than or equal to approximately 3 MΩ, or preferably less than or equal to approximately 1.4 M. However, it will be understood that different resistive switching components may have different optimum operating ranges.

Operating the devices in high ranges has an advantage of reducing the power dissipation. A more clear description of amount of power consumed when operated in high resistive state range is given in below. As described in supplementary note 2 described below, average power consumption can be estimated to be approximately 100 nW per channel, which is much lower than state-of-the-art values. For example, reducing the pulse width to 100 ns pulses, means that the power consumption may be reduced to approximately 10 nW per batch. Preparing the resistive switching components as described can configure the resistive switching components 20 to operate in higher resistive state regions. This is a characteristic of the $TiO_x$ material which may optionally be used for a resistive switching component 20. The operation of the resistive switching component 20 in higher resistive state regions may vary depending on the metal-oxide material used for the resistive switching component 20.

The method may further comprise applying an amplification and/or an offset to the output from the at least one sensor 10 such that a majority of the significant events in the input signal result in a voltage with a magnitude less than or equal to the upper threshold value. In other words, the method may comprise a step of altering the output from the at least one sensor 10 so that the resistive switching component 20 can properly respond to events in the signal within the volatile region.

For example, in order to decrease the magnitude of the voltage below the upper threshold value, a negative gain and/or an offset may be applied to the output from the neurological sensor 10 such that the voltage is less than or equal to the magnitude of the upper threshold value. Additionally or alternatively, in order to increase the magnitude of the voltage above the lower threshold value, a gain and/or an offset may be applied to the output from the neurological sensor 10 such that the voltage is greater than or equal to the magnitude of the lower threshold value. The method may comprise amplifying or reducing the output from the sensor 10. Additionally or alternatively, the method may comprise applying a voltage offset (which may be positive or negative) to the output from the sensor 10. The output may be amplified, reduced, and/or offset using a voltage modifying device 15 as depicted in FIG. 1. The voltage modifying device 15 may comprise an amplifying portion 15a (equivalent to an amplifier) which may amplify or reduce the voltage and/or an offsetting portion 15b (equivalent to an offsetting component). The amplifying portion 15a and the offsetting portion 15b may be provided integrally with one another in one device. The gain and/or the offset applied to the output should be selected carefully. The voltage of the signal may be adapted to have a magnitude greater than the lower threshold value for the majority of the time. However, it is also desirable to keep the voltage as less than or equal to the magnitude of the upper threshold value to avoid the resistive switching component 20 operating in the non-volatile regime (which might lead to saturation of the resistive switching component 20).

Different gains may be applied to the output of the sensor 10 to increase the voltage over the lower threshold value using the amplifying portion 15a of the voltage modifying device 15 and/or to decrease the voltage to less than or equal to the upper threshold using the amplifying portion 15a of the voltage modifying device 15. The voltage modifying device 15 may use the offsetting portion 15b to apply an offset to the output from the neurological sensor 10 which may for example, increase the voltage of the output or decrease the voltage of the output. The voltage modifying device 15 may comprise only the offsetting portion 15a, only the amplifier portion 15b, or both. Alternatively, separate components may be provided to apply the gain and offset, i.e. the portions 15a and 15b may be provided separately as an amplifier and an offset device rather than integrally as shown in FIG. 1. The order in which the gain and the offset are applied to the voltage may be selected by the user, i.e. the amplifier may be provided before the offset device or vice versa.

It will be understood that the magnitude of the upper threshold value may be specific to a particular device and may vary broadly. For example only, the upper threshold value may have a magnitude in the range of approximately 3.5V to 4.5V. The upper threshold value may be negative such that the range of the upper threshold value may be in the range of approximately −3.5V to −4.5V. It will be understood that the upper threshold value is a "soft-threshold" and is very approximate. This value is highly variable and may be very different between one resistive switching component and another, and for resistive switching components in different configurations.

Figure 2:
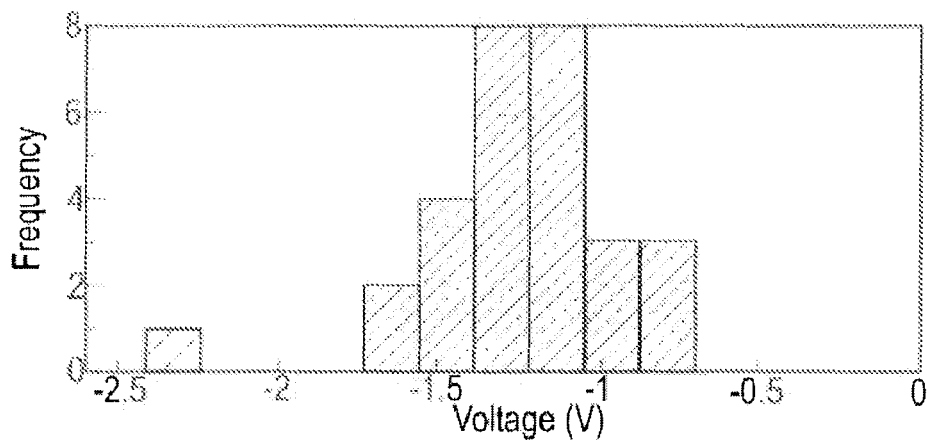
FIG. 2 depicts a range of lower threshold values for memristive devices in volatile region as extracted from 29 different devices.

As previously mentioned, the resistive switching component 20 may additionally, optionally, comprise a lower threshold value. FIG. 2 depicts a range of inherent threshold voltages (i.e. lower threshold values) for the resistive switching components (i.e. memristive devices) in the volatile region as extracted from 29 different devices. For example only, the lower threshold value may have a magnitude in the range of approximately 0.6V to 2.4V. The lower threshold value may be negative such that the range of the lower threshold value may be in the range of approximately −0.6V to −2.4V. It will be understood that the lower threshold value is a "soft-threshold" and is very approximate. This value is highly variable and may be very different between one resistive switching component and another, and for resistive switching components in different configurations.

As described, prior known devices can be formed to operate in a non-volatile regime. This means that the resistive state changes by in such a resistive switching component is retained for a certain period of time, the change can be retained indefinitely (at least until the device is reset). This differs from the spontaneous relaxation of the resistive state of the resistive switching component 20 of the embodiments described above. An example for preparing a resistive switching component which operates in the non-volatile regime is described here for information only. Preparing the resistive switching component may otherwise be referred to as electroforming and/or characterizing the resistive switching component to operate in a desired manner.

A way of carrying out electrical characterisation of a resistive switching component in a non-volatile regime is described here in detail. In the non-volatile regime, the resistive switching components can be electrically characterised in two stages. Initially, the resistive switching components undergo an electroforming step. This involves application of ramp of voltages on a pristine sample until a sudden, non-volatile change in the resistive state of the resistive switching component is observed. This typically occurs in the range of +6 to 8V[45] and the resistive switching component is then considered to be in low resistive state that is ON state. The resistive state of the resistive switching component decreases from 10's of MΩ to values in the range of 10 kΩ to 100 kΩ. Thereafter, in second stage a train of input programming pulses in alternating polarities can be applied, for example, at a fixed duration of 100 μs which leads to reversible resistive switching[50]. The resistive state of the device is read after each programming pulse at 0.5V. The resistive switching component can be switched to low resistive state (ON/SET state) and high resistive state (OFF/RESET state) with positive and negative polarity respectively after the applied stimulus exceeds the inherent threshold voltage of the resistive switching component. Importantly, the resistive switching components in non-volatile region gradually switch in 2 kΩ to 15 kΩ range. The response of the resistive switching component for one specific input stimulus can be fitted to a second order exponential function[45] indicating saturation of the resistive state of the resistive switching component due to continued operation. The resistive switching components may be asymmetric and demonstrate slightly different threshold for the resistive switching component for two different polarities. The inherent threshold voltage of the employed resistive switching components may vary in the range of approximately ±0.6-2.5V[45].

In an embodiment, the method described above further comprises preparing the resistive switching component 20 such that it operates in a volatile manner as described above. More particularly, the method may further comprise preparing the resistive switching component 20 such that the resistive switching component 20 is configured to spontaneously relax from the further resistive state towards or beyond the initial resistive state after the magnitude of the voltage subsequently falls. The resistive switching component 20 can be prepared to respond in a volatile manner as described in a variety of ways.

For example, the preparing may comprise applying a series of progressively increasing voltage pulses until a volatile resistive state change is defined. In more detail, specific ways of preparing the resistive switching device 20 are described below in further detail by way of example only. As above, the preparing may otherwise be referred to as electroforming and/or characterising the resistive switching component 20.

Optionally, the resistive switching component may be prepared such that the difference between the magnitude of the first threshold value and the second threshold value is greater than approximately 1V. It will be understood that this difference in magnitude is for example only and will depend on the specific resistive switching component 20 being used.

The preparing may comprise applying a series of progressively increasing voltage pulses until a non-volatile resistive state change occurs, such that the resistive switching component does not spontaneously relax after the magnitude of the voltage subsequently falls. As will be described in further detail below, after the non-volatile change occurs, the preparing may comprise a further step of applying a further series of increasing voltage pulses until a volatile resistive state change is defined. Thus, when preparing the resistive switching component 20 to act in a volatile manner, a non-volatile state change is used during the preparation steps of the resistive switching component 20. Preferably, the initial resistive state associated with the non-volatile resistive state change is greater than or equal to approximately 10 MΩ. Additionally or alternatively, the further resistive state associated with the non-volatile resistive state change is preferably less than approximately 10 MΩ, or more preferably, the further resistive state associated with the non-volatile resistive state change is less than or equal to approximately 5 M. Thus, a resistive state change when preparing the resistive switching component 20 is a non-volatile resistive state change and changes from being in a region above approximately 10 MΩ, to a region less than approximately 10 MΩ and preferably, changes to being in a region less than approximately 5 MΩ.

In an example, the method comprises electrical characterisation of the resistive switching component 20 in a volatile regime. In the volatile-regime, the resistive switching component 20 may undergo metastable memory state transitions following which resistive switching component 20 tend to relax from the further resistive state towards or beyond the initial resistive state within a predetermined time, more particularly, the resistive switching component 20 may relax to its equilibrium resistive state in a definite time window[42]. The resistive switching components 20 may be electrically characterised in two stages. A first electroforming stage is similar to the one described above in relation to electrical characterisation of a resistive switching component in a non-volatile regime. The first stage may thus comprise electroforming resulting in a non-volatile change which decreases the resistive state of the device from 10's of MQ to lower ranges which can be anywhere from approximately 0.1 MΩ to approximately 5 MΩ.

In an example using micro-devices, negative polarity pulses (which may be of the order of approximately −6V to approximately −8V, for example) may be used and in an example using nano-scale devices, positive polarity pulses (which may be of the order of approximately +4V to approximately +6V) may be used. Importantly, the resistive switching component 20 operating in a volatile region operate in much higher resistive state range then a resistive switching component 20 operating in a non-volatile region. For example, the resistive switching component 20 operating in the volatile region may operate in a resistive state range of approximately 300 kΩ approximately 3 MΩ region.

In a second stage, the resistive switching components 20 may be characterised using an algorithm developed specifically to test the volatility of the resistive switching devices 20. This is described in further detail for $TiO_x$ devices in relation to FIGS. 3a and 3b and FIGS. 4a and 4b described below.

FIGS. 3a and 3b relate to device architecture and electrical characterisation of the solid-state $TiO_x$ memristive devices in the volatile region. FIG. 3(a) Electrical characterisation of 200 nm×200 nm memristive device in the volatile region. An automatic volatility characterisation module capable of electrically characterising the devices in the volatile region is utilised. The module operates in two stages. In the first stage, the algorithm applies a series of progressively higher input stimulus of amplitude ($V_w$) and pulse width ($T_w$) to the target device following which the resistive state of the device is monitored at 0.2V. The module operates on a standard statistical two mean t-test condition and is terminated when the device reaches an equilibrium condition. In the second stage, the equilibrium condition is checked using the retention condition. Once the t-test is terminated the resistive state of the device is read for 60 s illustrated in small rectangles. In this case, the write pulses ($V_w$) are applied in the range of −0.2V--4V in steps of −0.2V. $T_w$ of the applied stimulus is 1 μs. FIG. 3(b) relates to aresistive state evolution of the DUT in response to the applied stimulus. The device operates in 600 kΩ-1.3 MΩ region.

Figure 4A:
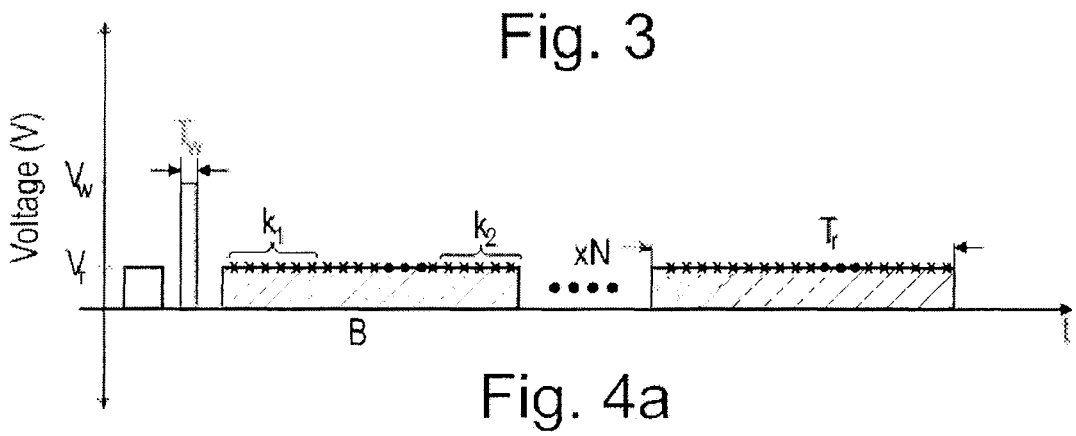
FIGS. 4a and b relate to a volatility characterisation algorithm.
Figure 4B:
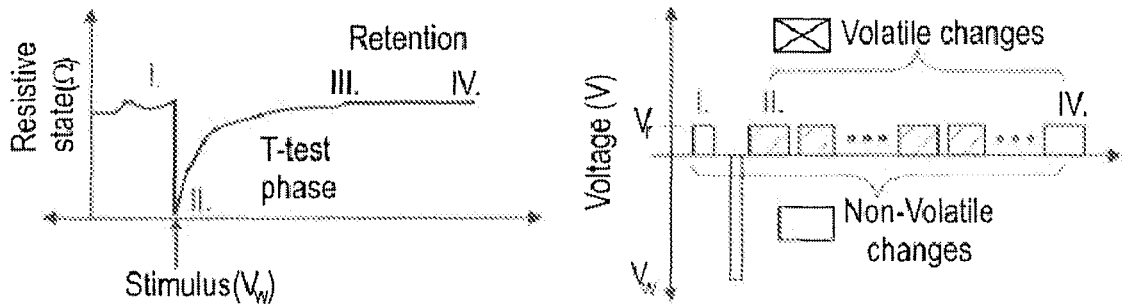

FIGS. 4a and 4b relate to a description of a volatility characterisation algorithm. The algorithm is applied in two stages. In the first stage, a series of progressively more invasive voltage pulses are applied and resistive state decay over time is monitored. In the second stage, the equilibrium condition is checked using the retention condition for 60 seconds. (a) Schematic for volatility module. The schematic describes the first stage for the volatility module. A programming pulse with amplitude and duration ($V_w$ and $T_w$) is applied on the device-under-test. Immediately afterwards, a read-voltage ($V_r$) of 0.2V is applied and the resistive state of the device is monitored using the standard two mean t-test in batches (B) with n measurements, where n is user-defined according to the equation 1. To estimate the output of t-test in each batch, the mean (μ) and the standard deviation (σ) of the first and last k-values are estimated. If the estimated value is less than the set threshold voltage (set as '1' in this work), the device is assumed to have been relaxed to its equilibrium state and the algorithm is terminated otherwise the next batch is applied and the same procedure is repeated until the device reaches a steady-state. 'τ' describes the overall time of the t-test. (b) Left Panel: Four major points for the assessment of the resistive state of the devices in the volatile module. T and 'II' is the measurement of the resistive state of the device before and after the application of the user-defined input stimulus. 'III' marks the termination of the t-test stage whilst 'IV' indicates the termination of the retention stage. Right panel: The estimation of the volatile (difference between the point IV and II) and non-volatile (difference between points IV and I) changes. The difference of volatile from non-volatile changes helps in determining the voltage range in which the devices can be safely operated in volatile region.

$$t = \frac{\mu_1 - \mu_2}{\sqrt{\frac{\sigma_1^2}{k_1} + \frac{\sigma_2^2}{k_2}}} \quad \text{Equation 1}$$

A module may apply a series of progressively more invasive pulses and then estimate the resistive state of the resistive switching component 20 using, for example, a standard two mean t-test method over a fixed interval of time. The t-test may capture the resistive state decay of the resistive switching component 20 over time and the module may terminate when an equilibrium state has been achieved. Subsequently, the t-test may be followed by a retention condition. In this test, the equilibrium state of the device may be checked for user-defined period of time. The output of the algorithm may determine the duration for the t-test required to achieve the equilibrium condition and the voltage ranges under which the resistive switching components 20 can be safely operated in the volatile region. These may be estimated by comparing the non-volatile changes with the volatile changes. This is described in relation to FIGS. 5a and 5b described below.

Figure 5A:
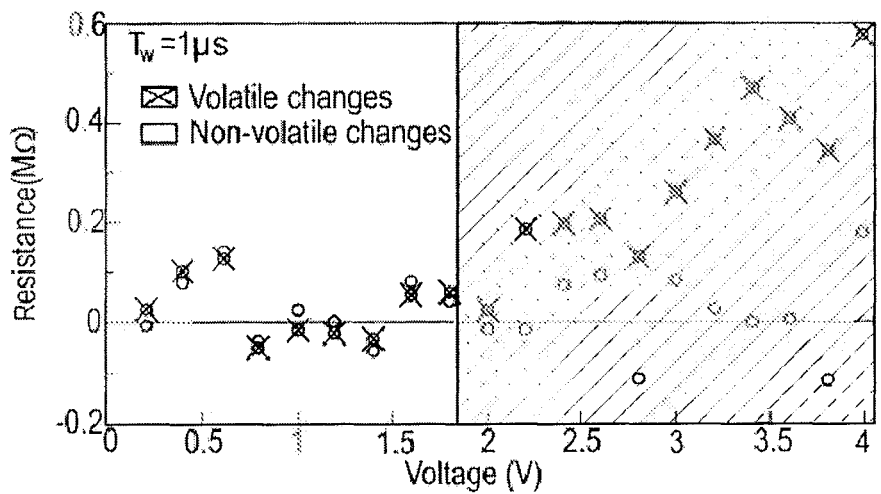
FIG. 5(a) shows a determination of an operating range of a resistive switching component being tested in a volatile region and FIG. 5b depicts volatility characterisation of exemplary $TiO_x$ nano-devices (200 nm×200 nm) using the volatility module described in FIGS. 4a and b.
Figure 5B:
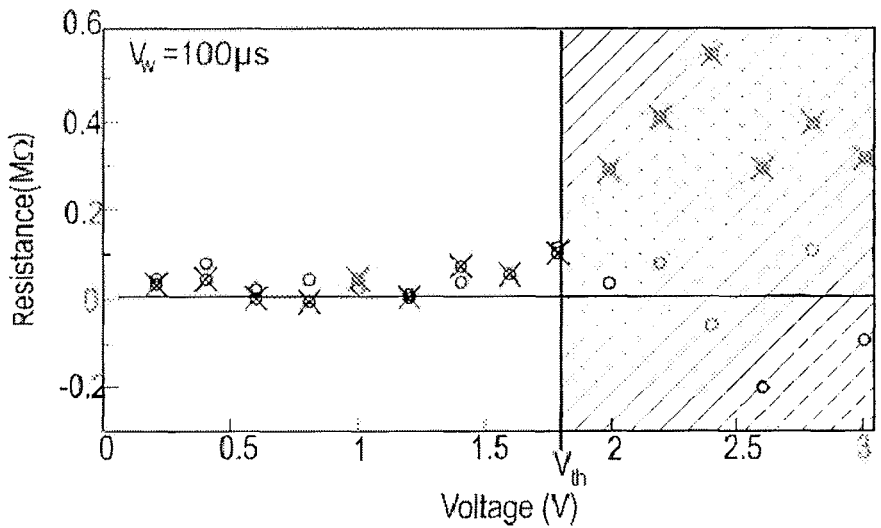

FIG. 5(a) shows a determination of the operating range of the DUT in volatile region. For every step of input stimulus applied, volatile and non-volatile resistive state changes are calculated indicated in circles with crosses and circles without crosses respectively. The grey band indicates the safe operation of the DUT in volatile region with approximately −1.8V being the threshold voltage of the DUT. FIG. 5b depicts volatility characterisation of the $TiO_x$ nano-devices (200 nm×200 nm) using the volatility module described in FIGS. 4a and 4b. Input stimulus was applied to the device-under-test in range of 0--3V in steps of 0.2V. The pulse width of the applied voltage was fixed at 100 μs.

Circles without crosses and circles with crosses indicate the non-volatile and volatile changes respectively. For the device-under-test the threshold of the device was found to be approximately −1.8V. The grey band indicates the region where the device can be operated in the volatile region.

Figure 6:
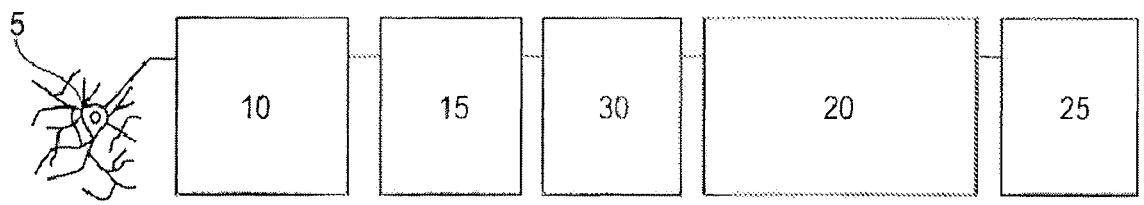
FIG. 6 depicts the system of FIG. 1 further comprising a transformation device.

The method may comprise a step of transforming the resistance of the resistive switching component 20. For example, a transformation device 30 may be provided. The transformation device 30 may be configured to encode a function or transform of the resistance of the resistive switching component 20. Such a transformation device 30 is depicted in FIG. 6. The transformation device 30 is shown as a separate device from the processing unit 25 and the resistive switching component 20, however, the transformation device 30b could be integral to the processing unit 25 or the resistive switching component 20. Additionally or alternatively, the transformation device 30 may be provided before the resistive switching component 20 and may be configured to encode a function or transform of the output of the sensor 10 (or the voltage modifying device 15). In other words, the transformation device 30 may apply a function or transform to the voltage before it is applied to the resistive switching component 20. Thus, the output is transformed prior to applying the output to the resistive switching component 20. For example, similarly to the function and transforms described above, the function or transform may use any derivative, integral or averaging operators, etc.

Some of the steps of the method may be implemented using electronic-based implementation. In other words, the method may be at least partially computer-implemented. This may include using software, hardware and/or firmware to implement some steps of the method. Additionally or alternatively, this may include using an integrated circuit and/or a printed circuit board and/or any other appropriate electronic circuit structure.

The present embodiment may provide a system 1 configured to carry out a method as described above including any of the optional/preferable features. For example, the present embodiment may provide a system 1 for detecting events in an input signal. The system 1 comprising a resistive switching component 20 configured to undergo a volatile resistive state change from an initial resistive state to a further resistive state when a voltage with a magnitude less than or equal to an upper threshold value is applied across the resistive switching component 20. Wherein the volatile resistive state change is such that the resistive switching component 20 spontaneously relaxes from the further resistive state towards or beyond the initial resistive state after the magnitude of the voltage subsequently falls. The system 1 comprises a processing unit configured to sample a further signal that is dependent on a resistance of the resistive switching component 20. The processing unit is further configured to identify, using the sampled further signal, a sequence of volatile resistive state changes corresponding to events in the input signal.

The resistive switching component 20 is configured to receive a voltage and undergo a resistive state change as described above when a voltage less than or equal to the upper threshold value is applied across the resistive switching component 20. Such a resistive switching component 20 allows the change of resistance over time to be determined and processed to obtain information about the neurological event.

Additionally or alternatively, the system 1 may further comprise at least one sensor 10 configured to measure the input signal and to output a voltage relating to the input signal. Thus, the sensor 10 may measure and output changes in voltage corresponding to events in the input signal. The sensor 10 may measures input signals, such as biological signals, or more particularly neurological signals, using electrodes, possibly micro-electrodes. Thus the sensor 10 may comprise at least electrodes which can be used in different ways, for example, in vivo or in vitro. Multiple sensors may be used, and may optionally be provided as part of an array. The sensor 10 may be a complementary metal-oxide-semiconductor (CMOS), and may be part of a CMOS multi-electrode-array (MEA).

The sensor 10 may store data relating to the voltage which may be passed to the resistive switching component 20 at a later date, or the sensor 10 may pass the data to the resistive switching component 20 in real time. Either way, the system 1 may optionally comprise an voltage modifying device 15 in order to increase the gain and/or offset of the voltage applied to the resistive switching component 20 as described above. The system 1 may comprise separate components to increase the gain and/or offset, e.g. an amplifier 15a and/or an offset device 15b as described above.

The system may comprise a transformation device such as 30, configured to transform the output from the neurological sensor 10 prior to the output being applied to the resistive switching component 20 as described above. Additionally or alternatively, the system may comprise a transformation device such as 30, configured to transform the resistance of the resistive switching component 20 as described above.

The system 1 may be a partially computer-implemented system 1. Thus, the system 1 may comprise at least one electrical computing device. The processing unit 25 may comprise or be part of such an electrical computing device. The electrical computing device may be any appropriate device such as a desktop computer, a laptop, a mobile device such as a phone, a tablet etc. The processing unit 25 may be part of a larger computer system with the ability to process large amounts of data due to the large amount of data generated in the present system 1. The processing unit 25 may include software, hardware and/or firmware to implement the methods described above. Additionally or alternatively, the processing unit 25 may include using an integrated circuit and/or a printed circuit board and/or any other appropriate electronic circuit structure.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. It is explicitly stated that all value ranges or indications of groups of entities disclose every possible intermediate value or intermediate entity for the purpose of original disclosure as well as for the purpose of restricting the claimed invention, in particular as limits of value ranges.

Figure 7:
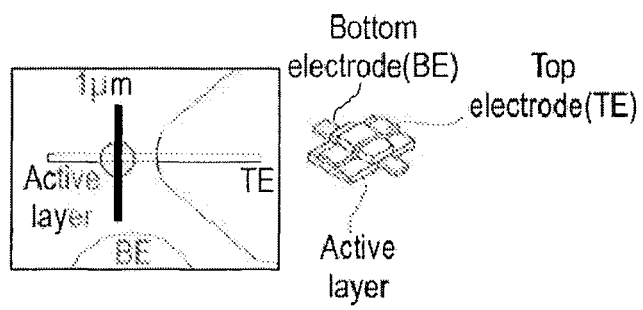
FIG. 7 depicts a schematic and a scanning electron Microscopic (SEM) image of a resistive switching component.

Detailed examples are provided below, which may relate to a sub 100 nW neural detector using volatile nano-metal-oxide memristors Operation of Memristors in Volatile Region Solid-state $TiO_x$ metal-oxide memristors with metal-insulator-metal architecture, as shown in FIG. 7 were fabricated on $Si/SiO_2$ substrate and are detailed in the Methods section (Device Fabrication). FIG. 7 relates to electrical characterisation of a solid-state $TiO_x$ memristive devices in the volatile region and shows a schematic and a Scanning Electron Microscopic (SEM) image of an employed memristive device.

Figure 8:
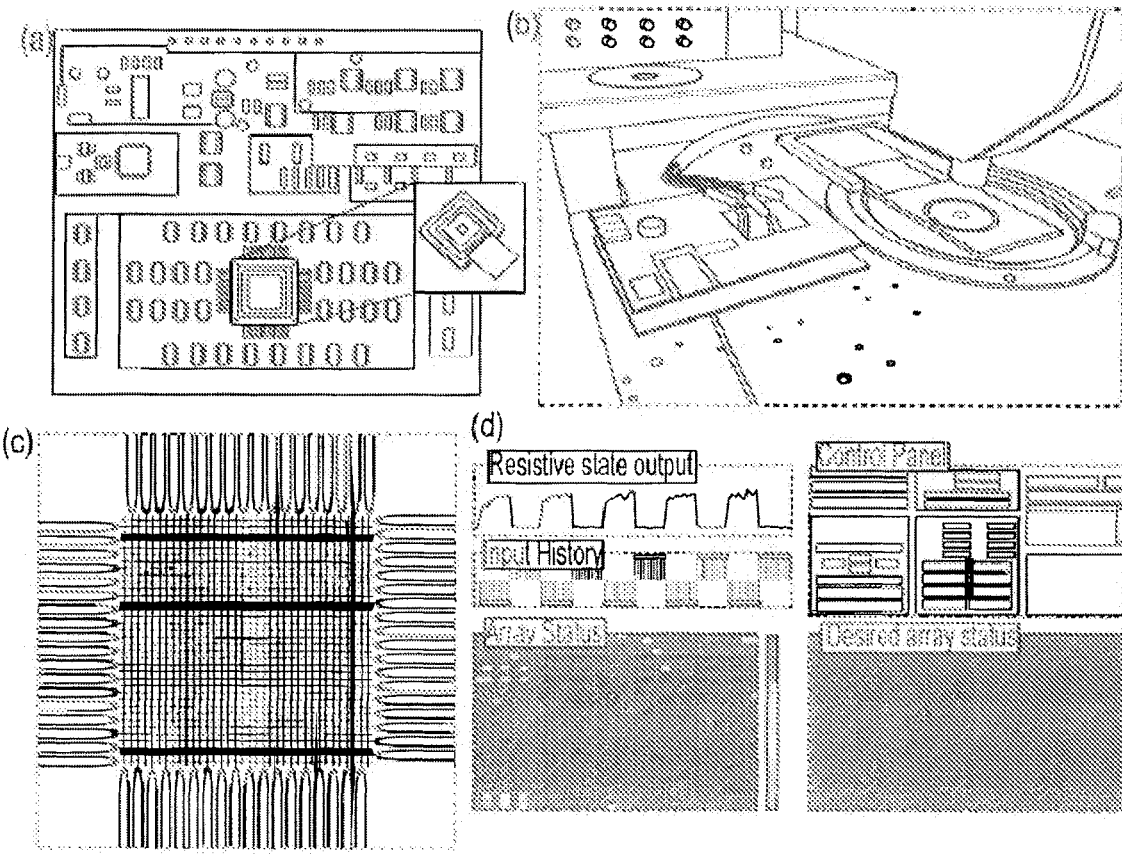
FIGS. 8a-d depict hardware infrastructure used in order to implement a proposed biasing protocol in an memristive integrating sensor (MIS) platform.

A custom-made hardware infrastructure was used for the electrical characterisation of fabricated devices, which are examples of resistive switching components 20 described above (see Methods, Hardware Infrastructure and FIG. 8). FIG. 8 depicts hardware infrastructure used in order to implement the proposed biasing protocol in the MIS platform. (a) Illustration of the custom-made hardware developed in order to facilitate en-masse electrical characterisation of the fabricated memristive devices[49,50]. The circle indicates the position of inserting the wire bonded packaged memristive devices. (b) On-wafer testing of the memristive devices using a probe card used as a communication channel between the mBED board and the wafer. At one point of time approximately 1000 devices fabricated in crossbar architecture or 32 devices in stand-alone configuration can be interfaced using the developed testing technology. (c) Illustration of the probe card needles touching down on one of the crossbar configurations. (d) Graphic user interface (GUI) supporting the hardware infrastructure. GUI can be used for programming the biasing protocols applied to the memristive devices and the status of the devices can then be tracked in real-time.

The devices can be subjected to a high voltage stress until there is a sudden non-volatile change in the resistive state of the DUT known as 'electroforming'[38,45]. In normal operation, the devices can be operated in non-volatile[45] or volatile region critically dependent upon the polarity of the voltage stress applied during the electroforming procedure. Importantly, the devices may feature inherent bipolar thresholds levels below which voltage is too weak and there is no change in the resistive state of the device (which corresponds to the lower threshold value) and above which there are gradual, persistent resistive state transitions (which corresponds to the upper threshold value). This property is exploited in traditional MIS technology with neural recordings wherein the memristive devices are operated in the non-volatile region (see FIG. 9). The supra-threshold events are encoded in the gradual non-volatile resistive state transitions whereas the sub-threshold events i.e. noise is inherently suppressed. The electrical characterisation for the devices in the non-volatile region is described above and in the methods section.

Figure 9:
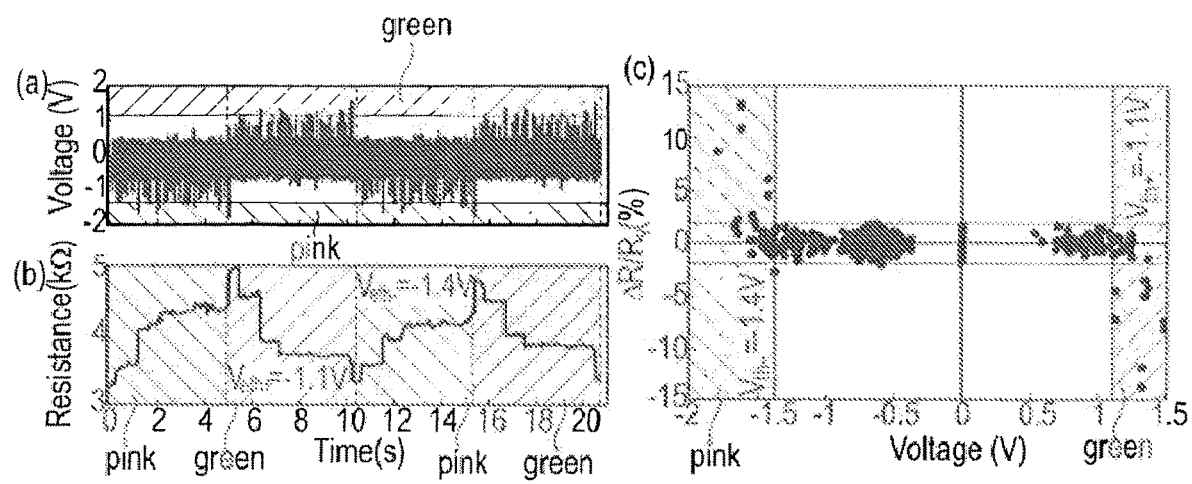
FIGS. 9a-c depict operation of exemplary $TiO_x$ devices in non-volatile region.

FIG. 9 depicts operation of specific examples of the resistive switching components 20 described above, such as $TiO_x$ devices, in the non-volatile region[45]. (a) A single neural recording is concatenated four times alternatively in opposite polarity. The selected neural recording was processed in MATLAB to invert the polarity. The green and pink band in the figure indicates the extracted threshold of the device-under-test (i.e. of a tested resistive switching component 20). The G and $V_{off}$ value for this specific neural recording was set to 2.8 and 0, respectively. (b) Response of the device-under-test in response to the neural recording in (a). In response to the negative (positive) supra-threshold events there is gradual increase (decrease) in the resistive state of the device. The same phenomenon can be seen over the illustrated four cycles. Notably, the supra-threshold events are encoded in the resistive state changes of the devices. The threshold for the two polarities is slightly different indicating inherent asymmetry in the devices which is typical of this device family. (c) The resistive state changes in each bin are plotted as a function of the highest voltage magnitude in each bin. On x=0 axis, the agglomerated changes are indicative of the noise measurements made at the end of each batch. These measurements are used to set the noise band marked by the grey band. Anything falling in this band is considered to be 'insignificant' and everything outside this band is considered to be a 'significant' change and is estimated as the spike estimated by the MIS platform.

Devices in volatile region undergo metastable resistive transitions in much higher resistive state range and are chiefly capable of inherent self-resets thus making manual resets redundant. A volatility characterisation module was developed to automatically characterise the devices in volatile region (see Methods, Device Electrical Characterisation in Volatile regime and FIGS. 4a and 4b), which relates to preparation of the resistive switching component 20 described more generally above. In principle, the module applies series of progressively more invasive voltage pulses and then monitors the resistive state of the DUT (resistive switching component 20) at fixed read-out voltage over time as shown in FIGS. 3a and b. The module may use statistical standard two mean t-test to record the resistive state decay over time and terminates when the devices relaxes back to an equilibrium condition. Importantly, the algorithm makes no assumption on what the equilibrium state should be. The equilibrium state may be the initial resistive state before an event and optionally, may be substantially constant. Thereafter, the achieved equilibrium condition is checked using a retention condition implemented for user-defined time window (for instance 60s in FIG. 3b). The output of the volatility module helps in determining the range in which the devices can be safely operated in the volatile region and provides a rough estimate of time taken by the devices to reach an equilibrium state.

Notably, as shown in FIGS. 3a and b, the operating resistive state region of the DUT is from approximately 700 kΩ-1.4 MΩ and the results are demonstrated using negative as the dominant polarity with 1 μs pulse width (see FIG. 5b for 100 μs pulse width). The output of the volatility module is determined by estimating resistive state changes between the steady state attained after the completion of the retention stage and the resistive state measurements taken immediately before and after the applied voltage stimulus, i.e. immediately before and after the voltage applied across the resistive switching component 20 as previously described. This results in estimation of non-volatile and volatile changes respectively, as shown in FIG. 5a. Evidently −1.8V marks the approximate threshold voltage of the DUT above which the device exhibits volatile changes in the region from −1.8V to −4V. On the contrary, the resistive state changes in the sub-threshold region are considered as insignificant and are mainly attributed to the background fluctuations caused due to the measurement of noise. The range of inherent threshold voltages for the employed $TiO_x$-based memristive devices varies in the range of approximately −0.6V to −2.5V (see FIG. 2).

Estimated volatility characterisation parameters are subsequently used in pre-processing of the neural recording waveforms in the MIS platform. The schematic for the MIS platform is illustrated in FIG. 10*a* and an overall picture of the MIS system including the front-end system is presented in FIGS. 10*b-d*.

Figure 10A:
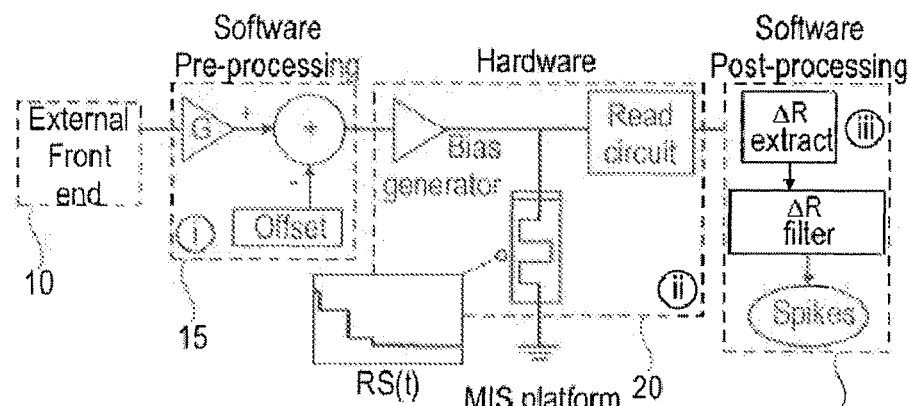
FIGS. 10a-d depict more detailed views of the system of FIG. 1.
Figure 10B:
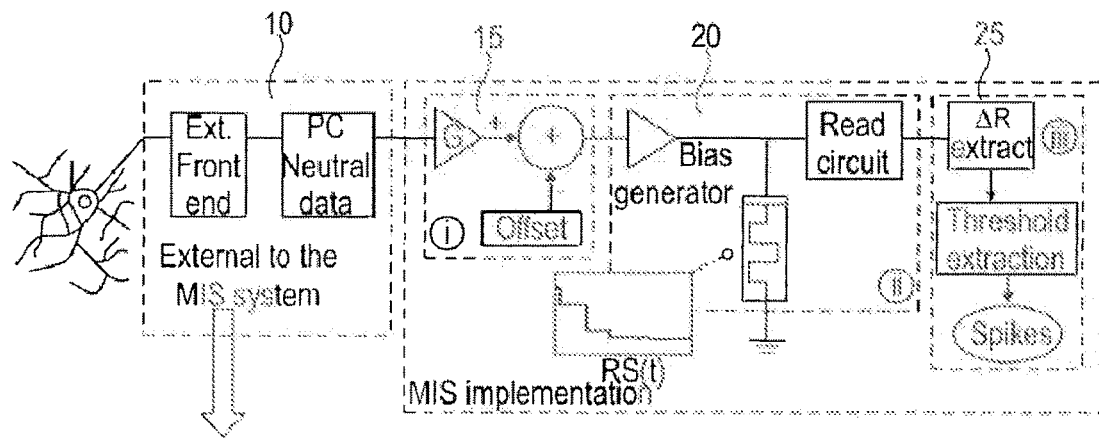
Figure 10C:
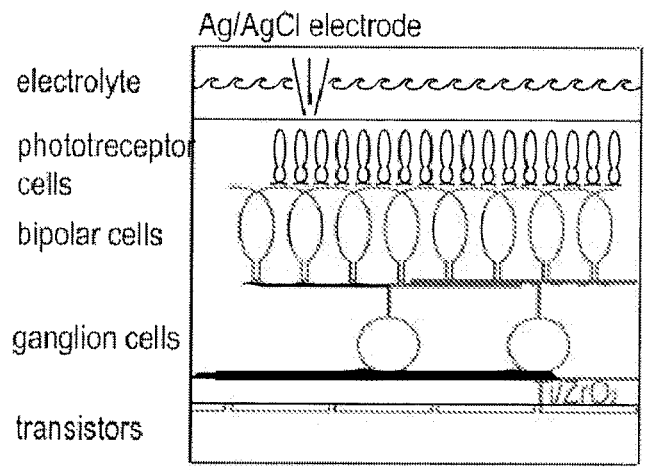
Figure 10D:
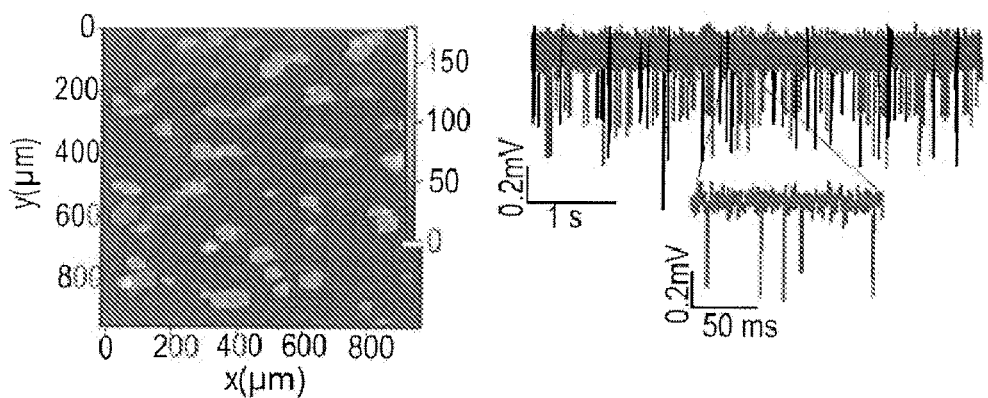

FIG. 10*a* depicts a schematic for the implementation of a Memristive Integrating Sensor (MIS) platform. The dashed box indicates the external front-end CMOS-based MEA from which the neural recordings are obtained. The MIS platform consists of three stages: (i) The recorded neural data is pre-processed using a gain (G) and offset ($V_{off}$) stage. (ii) The processed neural recordings are then used to bias the target memristive device using the hardware infrastructure. The resistive state of the device is read periodically. (iii) The compressed resistive state measurements are processed offline and the significant resistive state changes are filtered-off from the insignificant ones. The significant resistive state changes are estimated as spikes in the output of the MIS system. The MIS system may be considered to be system 1 described above without necessarily including the sensor 10. FIG. 10*b* depicts an overall block diagram for the memristive integrating sensors (MIS) platform. FIG. 10*b*: Block diagram highlighting the fact that in this work the implementation of MIS platform indicated by the black dashed line is external to the Complementary Metal Oxide Semiconductor (CMOS) Multi Electrode Array (MEA) neural recording system[35,4,5]. The extracellular recordings obtained from the rabbit retinal ganglion cells using CMOS MEA that is termed as 'front-end' and is stored on to a PC. These recordings are acquired and processed using the MIS platform. As illustrated in FIG. 10*b* in the first step the recordings are suitably amplified using a 'gain (G)' and 'offset ($V_{off}$)' stage (i). The pre-processed recordings are then used to bias the memristive devices using the hardware infrastructure described in FIG. 8, where the resistive state of the device is read periodically (ii). The compressed read-out states are processed offline and the spikes detected by the MIS system are estimated (iii). FIG. 10*c* Image of the retina/chip configuration in the employed CMOS MEA atop which the slices from the mid-peripheral of the rabbit retina are placed and measured directly. The transistors are separated from the cell layer using a thin Ti/ZrO$_2$ insulating layer. FIG. 10*d*: (Left) Surface plot of the electrical activity from tissue slices placed atop the CMOS MEA. (Right) Blocks of neural activity (voltage-time series) in hundreds of mV range obtained from the front-end system.

The neural recordings were obtained from slices of mid-peripheral rabbit retinal ganglion cells placed above an external front-end CMOS based MEA (see Methods, 'Front-end neural recording system CMOS Multi Electrode Array'). Importantly, in this work there was no modification performed on the front-end system and was kept completely external to the MIS platform. Neural recordings are essentially voltage-time series in the range of ±0.5V. The front-end system outputs block of neural recordings containing approximately 63 k samples recorded at a sampling rate of 12.2 kHz. In the MIS platform, in the first stage ('i'-FIG. 3*a*) the signals are pre-processed using a suitable Gain (G) and Offset ($V_{off}$) value. The neural signals are amplified such that the spikes in the neural waveform are above the threshold and the noise is below the threshold of the DUT.

These pre-processed neural recordings are then passed through the memristive devices in batches ('ii'-FIG. 3*a*) and the resistive state of the DUT is read periodically in real-time. In this work, we follow a standard schematic for signal processing. In a batch of thousand data points, the resistive state of the DUT is recorded at the beginning of each batch, then every 300 points and finally at the end of each batch. This leads to segmentation of the neural data in each batch into smaller bins. Consecutive measurements in each batch are used to estimate the resistive state changes whilst one resistive state change measurement taken at the end of each batch and the beginning of next batch with no interceding neural data points is used to estimate noise or reference data values (see Methods, 'Neural recording biasing strategy' and FIG. 11). Finally, the compressed resistive state changes are then processed offline and compared to the noise measurements ('iii'-FIG. 3*b*). The significant resistive state changes (in comparison to the noise measurements) are estimated as spikes and the insignificant resistive state changes are discarded.

Figure 11:
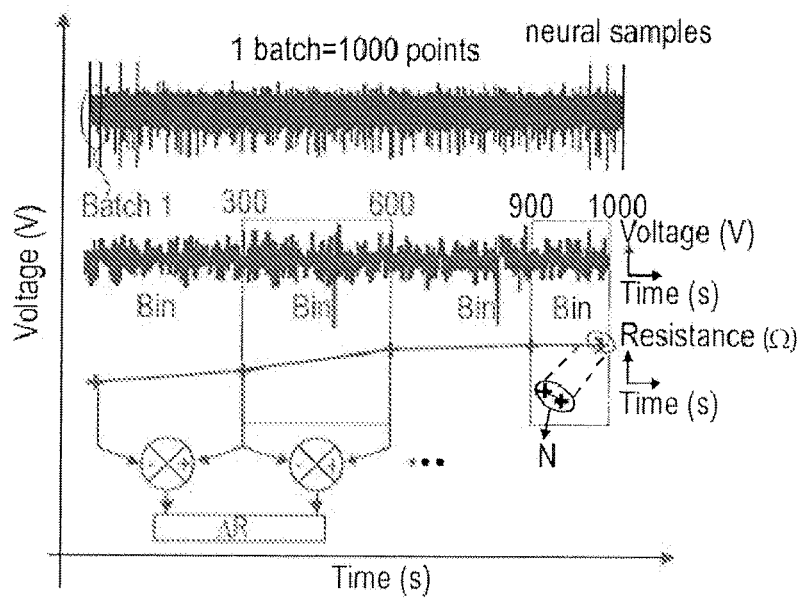
FIG. 11 depicts a signal processing methodology in the MIS platform.
Figure 14:
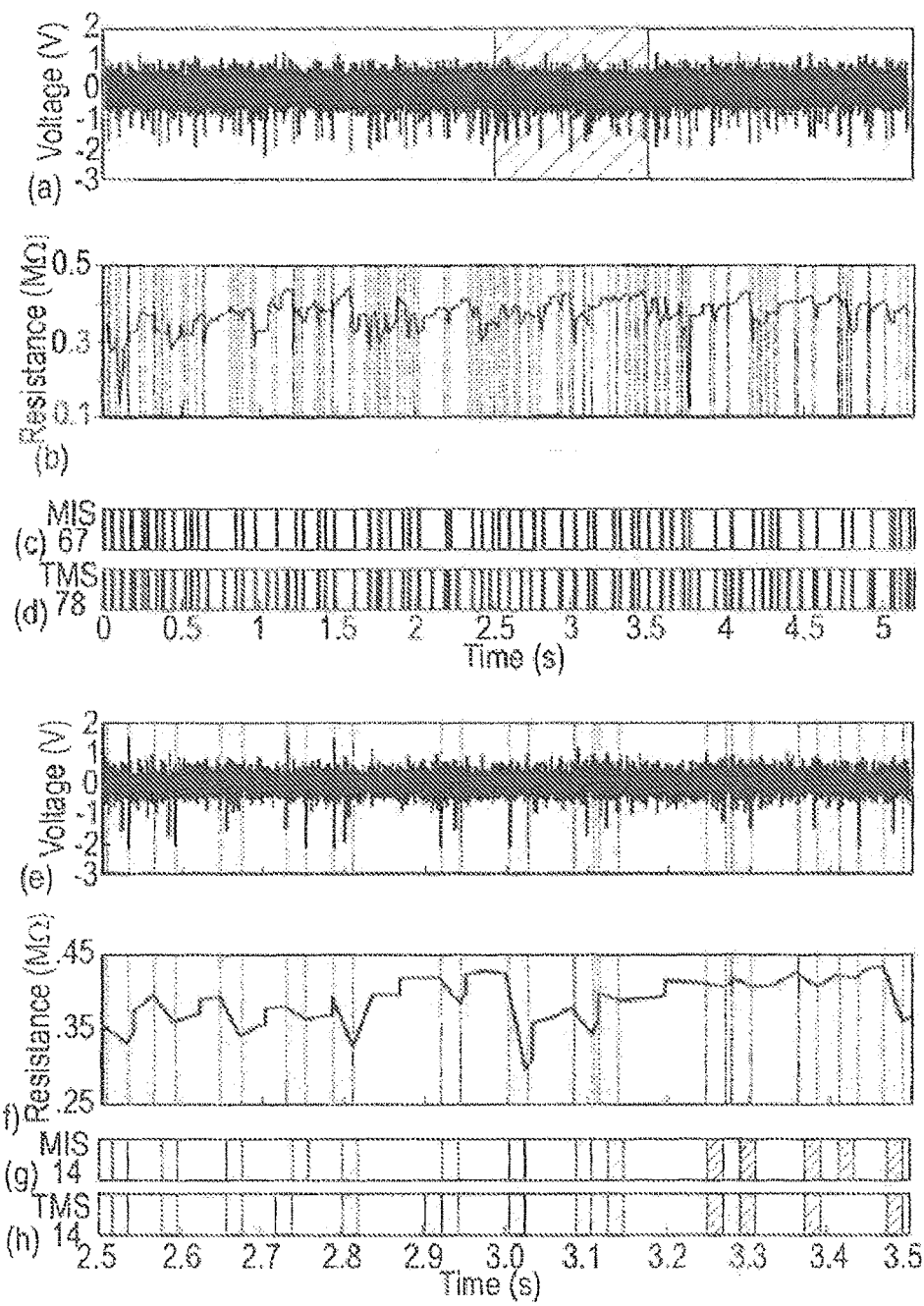
FIGS. 14a-h depict biasing of exemplary 60 μm×60 μm $TiO_x$ devices using a neural recording in the volatile region.

FIG. 11 depicts a signal processing methodology in the MIS platform. Every block of neural recording obtained from the 'front-end' system is approximately 63 k samples. The neural data after suitable amplification using the G and $V_{off}$ stage is fed to the memristive devices in batches of 1000 data points. In every single batch (1000 data points) the resistive state of the device is assessed five times in smaller bins that is in the beginning of each batch and then after every three hundred points. For instance, in the first 1000 neural data points, the resistive state is read after 300, 600, 900 and 1000$^{th}$ point. These consecutive measurements are used to estimate the resistive state changes in each bin. Notably, the neural recording is paused during the reading of the resistive state of the device. Following this, one measurement is taken at the end of each batch and the beginning of the next batch with no neural data in between and this measurement is used to estimate the Noise (N) in the system. N can arise due to measurement uncertainties of the employed devices or due to measurement board. Hence, the described methodology transforms 63 k neural data points into 316 resistive state measurements containing consecutive and noise measurements and the data is thus compressed by a factor of 200. Thereafter, the resistive state measurements are post-processed to estimate the resistive state changes. Significant resistive state changes (explained in FIGS. 12*a* and 12*b*) are estimated as spike count of the MIS platform.

FIGS. 12*a* and 12*b* depict a comparison of the Noise band diagrams in the volatile and non-volatile region of operation. (a) Noise-band diagram settings in the non-volatile region. Normalised plot of resistive state changes ($\Delta R/R_0$) in each bin is plotted as a function of maximum voltage magnitude in each bin. The noise-band (horizontal band marked) is estimated using the noise band measurements made at the end of each batch and the beginning of next batch with no interceding neural data points (as explained in FIG. 11). (b) Assuming Gaussian distribution, mean and the standard deviation are estimated. 6 sigma method is chosen to set the boundaries of the noise-band. The estimated resistive state changes falling within this band are discarded as this cannot be differentiated from the noise band measurements. Everything outside this band is estimated to be a significant change and is estimated as a spike in the output of the MIS platform. The existence of the threshold voltage classifies the resistive state changes in four groups. In a simple threshold detector, everything above the threshold is estimated as a spike and everything below is discarded as noise. However, because of the existence of noise-band in the MIS platform, the data is quantified as follows: Outside the noise band and below $V_{th-}$: True Positives (TP), outside the noise band and above $V_{th-}$: False Positives (FP), inside the noise band and below $V_{th-}$: False Negatives (FN), inside the noise band and above $V_{th-}$: True Negatives (TN).

The results are benchmarked against the established template matching system and the quantification parameters are redefined. TP (TN) indicates when the two system agree (disagree) for the presence of spike. FP indicates a spike detected by the MIS system and not by the TMS system. FN indicates a spike indicated by the TMS system and not MIS system. Importantly, in this work we assume template matching system to be a perfect spike detector. The rate of TP (TPR) and FP (FPR) are estimated using the following equations:

$$\text{Rate of } TP = \frac{TP}{TP+FN}$$
$$\text{Rate of } TP = \frac{FP}{FP+TN}$$

(c) Noise-band diagram in the volatile region. For the experiments with neural recordings in the volatile region most of the significant spikes are present in the negative polarity. Noise measurements are marked using a grey dashed eclipse indicating the spread of measurements which notably is inclined in the positive polarity. During the operation of the device in the volatile region, the significant resistive state changes due to supra-threshold spikes are in the negative quadrant. This is due to the fact that the metastable resistive state transition is to a low resistive state following which the device intrinsically resets to a higher resistive state. Hence, for the noise band boundary settings in the volatile region, the noise band measurements in the positive polarity are discarded (that is switching of the device-under-test back to high resistive state) and only the measurements in the negative polarity are used. The boundary is set using the 4-sigma method which is indicated by the horizontal dashed line. The dashed line on the vertical axis indicates the threshold voltage dividing the resistive state changes in four quadrants i.e. TP, FP, FN, TN. Again, the quantification and benchmarking of the results against the template matching method is carried out using the equations described in (b).

Volatile MIS Neural Detector $TiO_x$-devices, which are examples of resistive switching components 20, can be operated using the pre-processed neural recordings in the MIS platform once the operating region of the memristive devices (resistive switching components 20) is determined using the volatility characterisation algorithm. The neural recording, i.e. the input signal, chosen for the experiment contains dense spiking pattern as illustrated in FIG. 13a. FIGS. 13a-e depict spike-detection of the MIS system in the volatile region and benchmarking of the results against the TMS. (a) Neural recording used for biasing the DUT. Gain (G) and offset ($V_{off}$) values in this experiment were fixed at 3.2 and 0, respectively. (b) Resistive state evolution of the DUT with time in response to the neural recording in (a). Time interval where the MIS system detects spikes are indicated in grey. (c) and (d) Total number of spikes detected by the MIS and TMS that is 67 and 78, respectively represented in black colour. (e) Normalised changes in the resistive state of the device ($\Delta R/R_0$) in each bin are plotted as a function of highest voltage magnitude in each bin. The resistive state measurements in the yellow eclipse represents the noise measurements made at the end of each batch and beginning of the next batch with no neural feed. The inset represents the histogram for the noise measurements. The dashed line on the horizontal axis represents the boundaries of the noise band estimated using the 4-sigma method that is mean (0±2*standard deviation (a) whilst the band indicates the significant resistive state changes as detected by the MIS system. Threshold voltage ($V_{th-}$) divides the resistive state changes in four quadrants indicating the True Positives (TP), False Positives (FP), True Negatives (TN) and False Negatives (FN). On benchmarking these values against the TMS, the rate of TP (TPR) and FP (FPR) are estimated.

The operational parameters i.e. gain and offset values used for pre-processing of the neural recording were fixed at 3.2 and 0, respectively. The choice of the operational parameters is dependent on the estimated approximate threshold voltage of the DUT using the volatility characterisation module. On biasing the target device with the neural recording the intrinsic reset capability of the DUT can be clearly noted in FIG. 13b. For instance, the initial resistive state of the DUT is approximately 350 kΩ following which the device demonstrates metastable resistive state transitions to a low resistive state in response to the supra-threshold events. The relaxing back of the device from low resistive state to high resistive state are inherent resets illustrating the volatile nature of the employed devices. The close-ups of the FIG. 13a, b in window 2.5 s-3.5 s are presented in FIGS. 14a-h to illustrate this point more clearly.

FIGS. 14a-h depict biasing of exemplary 60 μm×60 μm $TiO_x$ devices using a neural recording in the volatile region. (a) Neural recording used for the biasing of the device-under-test. (b) Resistive state evolution of the device-under-test with time. (c) and (d) Spikes (i.e. events) detected by the MIS platform (67) and TMS (78) respectively. (e) and (f) Close-up of the neural recording employed in (a) and the resistive state evolution in (b) for time window 2.5 s-3.5 s, respectively. (g) and (h) Spikes (i.e. events) detected by the MIS and TMS system, respectively. In the close-up window the two systems agree for majority of instances except the point marked by '*'. The grey band indicates the bins with significant resistive state changes estimated as spikes in the output of the MIS platform. The quantification parameters for this specific recording are as follows: TP, FP, TN and FN are 58, 9, 166 and 20 respectively. The rate of TP (TPR) and FP (FPR) for this specific recording is estimated to be 74.3 and 5.14 respectively.

Spikes are estimated after post-processing of the resistive state measurements obtained using the standard schematic described in the methods section ('Neural recording biasing strategy'). As shown in FIG. 13e, resistive state change ($\Delta R/R_0$) in each bin is plotted as a function of highest voltage magnitude in each bin. Noise measurements are used to differentiate significant resistive state changes from the insignificant ones. The inset of FIG. 13e represents the histogram for the noise measurements indicating an excessive inclination towards the positive polarity. Since the negative polarity is used as the dominant polarity and the intrinsic reset transitions are in the positive polarity, the noise measurements in the positive polarity are completely discarded and only the measurements in the negative polarity are used to estimate the legitimate noise band boundaries (see Methods, Neural signal processing through MIS platform and FIGS. 12a to c). Noise band boundaries are estimated using only negative polarity noise measurements with the 4-sigma method (assuming Gaussian distribution), as shown by the horizontal dashed line in FIG. 13e. Everything outside this band in the negative region is estimated to be significant and is computed as a spike whilst everything inside this band is considered as an insignificant resistive state change and is discarded. Following this methodology, the total number of spikes detected by the MIS system in FIG. 13c is equal to 67.

Figure 15:
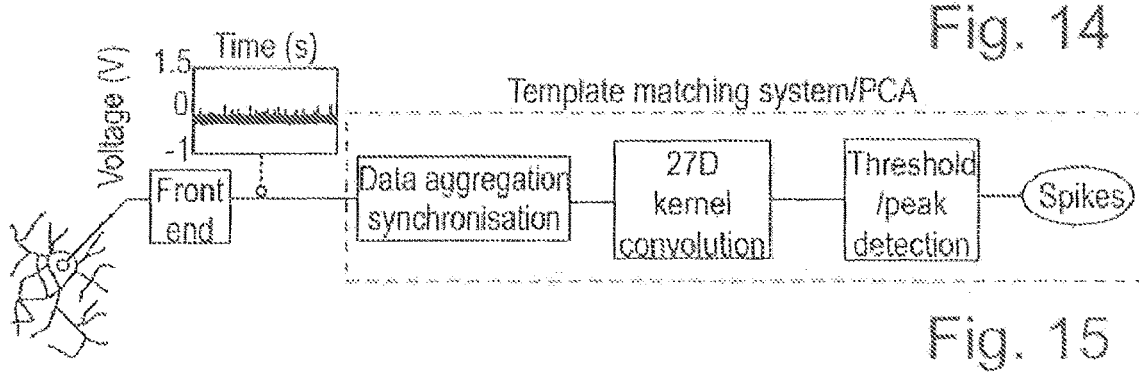
FIG. 15 depicts a schematic of the Template Matching System (TMS) used as a benchmarking standard for a proposed MIS platform.

The outcome of the MIS platform is benchmarked against the established state-of-the-art template matching system (TMS, see FIG. 15). FIG. 15 depicts a schematic of the Template Matching System (TMS) used as a benchmarking standard for the proposed MIS platform. The same front-end system as described in FIG. 10b is used to acquire the neural data. The data in this system is processed through computationally heavy Principal Component Analysis (PCA) technique[4].

As shown in FIG. 13d, the total number of spikes determined by the TMS is equal to 78. In FIG. 13e, at approximately −1.5V the resistive state changes are divided in four quadrants i.e. True Positives (TP) and True Negatives (TN): indicating the agreement and disagreement between the two systems respectively, False Positives (FP) and False Negatives (FN): indicating detection of spikes only by MIS and TMS system respectively. These quantification parameters are used to calculate the sensitivity of the system also called as the true positive rate (TPR) and the false positive rate (FPR) (Methods section, 'Neural signal processing through MIS platform') Assuming TMS to be a perfect spike detector the two values are estimated to be 74.35% and 5.14% respectively. These values are much higher in comparison to the non-volatile region, for example, for the same neural recording in FIGS. 16a-c, depicts TPR and FPR after introducing optimised manual frequent resets is equal to 60% and 30% respectively.

Figure 16:
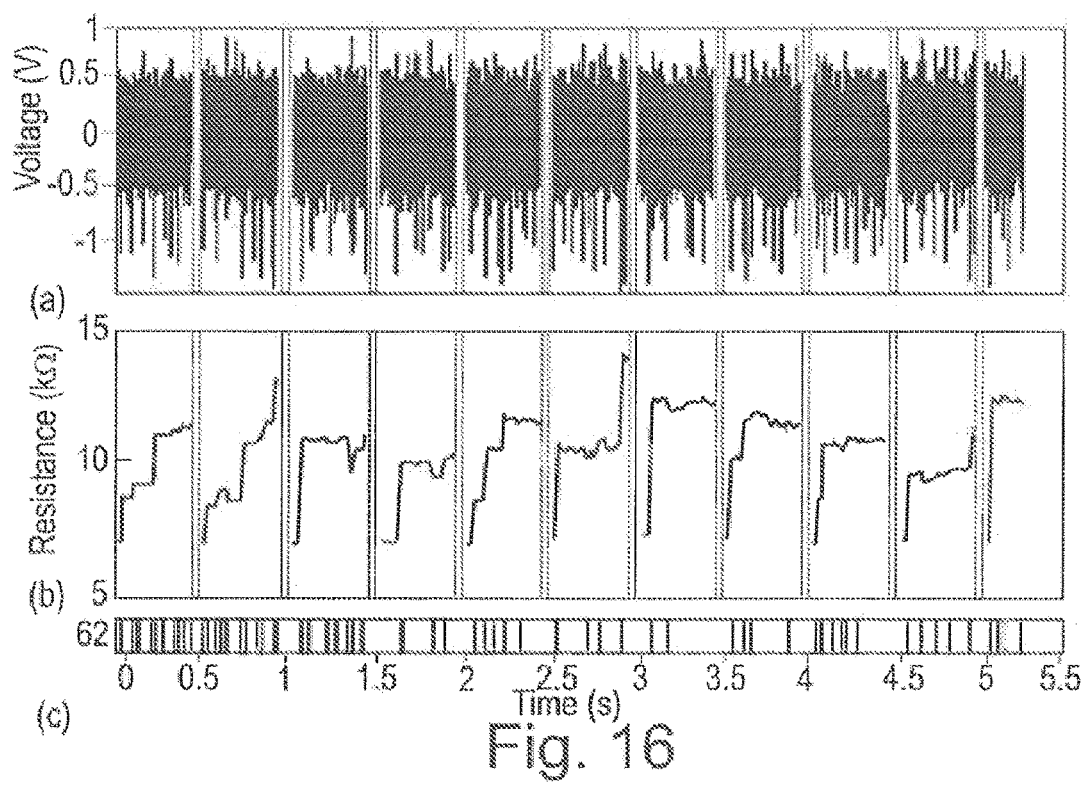
FIGS. 16a-c depict true positive rates and false positive rates after introducing optimised manual frequent resets.
Figure 17:
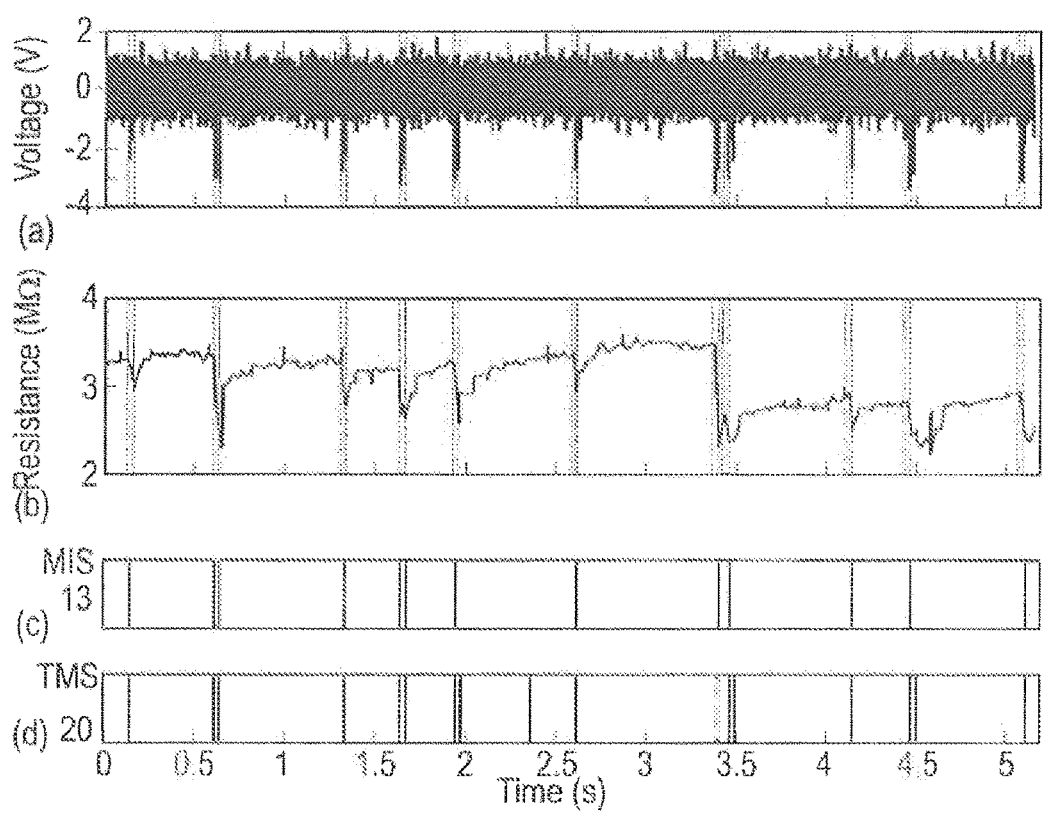
FIGS. 17a-d relate to robustness of $TiO_x$ devices.

FIGS. 16a-c depict manual frequenting of the memristive devices in the non-volatile region[39]. The continued operation of the device in a single polarity leads to the saturation of the resistive state of the device. As a mitigation strategy, the neural recording of approximately 63 k data points is sliced into smaller sub-neural recordings with approximately 6 k data points. Grey bands indicate the separation regions, as shown in (a). (b) Resistive state response of the DUT in correspondence to the sub-neural recordings with time. After every sub-neural recording the device is manually reset to its initial resistive state represented in yellow bands with a pulse of positive polarity of 100 μs. The initial resistive state of the device is in the region of 6-8 kΩ and the operation of the device is in the region of 6 kΩ (low resistive state) to 15 kΩ (high resistive state). (c) The total spike count of the MIS system is 62 represented as bins.

The concept of volatile MIS in FIG. 13 was validated using memristive device of dimensions 60 μm× 60 μm. The robustness of the devices for the same dimensions is illustrated in FIGS. 17a-d. A neural recording with significantly different spiking pattern in comparison to FIG. 13a was used to bias a memristive device. TPR and FPR in this case was equal to 65% and 0%, respectively. Besides, similar results from fifteen different devices are tabulated in Table 1 (FIG. 21) and the highest TPR and FPR obtained is equal to 88.4% and 13% respectively.

FIGS. 17a-d relate to robustness of $TiO_x$ devices. Biasing of 60 μm×60 μm devices using a different neural recording in comparison to the one presented in FIGS. 14a-h in the volatile region. (a) Neural recording used for the biasing of the device-under-test. (b) Resistive state evolution of the device-under-test with time. (c) and (d) Spikes detected by the MIS platform (13) and TMS (20) respectively. The grey band indicates the bins with significant resistive state changes estimated as spikes in the output of the MIS platform. The quantification parameters for this neural recording are as follows: TP, FP, TN and FN are 13, 0, 233 and 7 respectively. The rate of TP (TPR) and FP (FPR) is found to be 65 and 0 respectively.

Table 1 (FIG. 21) relates to robustness of $TiO_x$ memristive devices. For this experiment, devices with different dimensions i.e. 60 μm×60 μm and 200 nm×200 nm and different neural recordings with significantly different spiking pattern were used. For the pre-processing of the neural recording, the operational parameters that is G and $V_{off}$ were varied. The quantification parameters are indicated in the table with the estimated rate of true positives and false positives. MIS: Memristive Integrating Sensors System, TMS: Template matching system, TP: True Positives, FP: False Positives, TN: True Negatives, FN: False Negatives.

Nano-Scale Volatile MIS Neural Detector

Memristors offer huge advantage in terms of scalability and can be accommodated in Back-End-Of-Line (BEOL) of CMOS technologies thus immensely benefiting future implantable neuroprosthetic platforms. We further justify the MIS concept with highly downscaled memristive devices of dimensions equal to 200 nm×200 nm. The devices were fabricated using the fabrication procedure described in the methods section (see Device Fabrication). For the validation of the nano-memristors as MIS elements, we used the same neural recording with the same spiking pattern as shown in FIG. 13a and benchmarked the obtained results against the TMS. The neural recording was amplified using G and $V_{off}$ values of 2.6 and −0.6 respectively as illustrated in FIG. 20a.

FIGS. 20a-h relate to Scalability of the $TiO_x$ devices to the nanoscale dimensions and operation of nano-devices as MIS elements. (a) The employed neural recording pre-processed using gain and offset value of 2.6 and −0.6 respectively. The pink band indicates the inherent threshold voltage (lower threshold voltage) of the DUT. (b) Resistive state changes in the target DUT in response to the neural data in (a). The dimensions of the nano-devices used for this experiment are 200 nm×200 nm. The threshold voltage of the DUT is −1.3V. (c), (d) Total number of spikes detected by the MIS and TMS system is equal to 78 for both the systems. The black bins indicate the spike positions. (e) and (f) are close-ups for the neural recording and the resistive state evolution shaded grey in (a) and (b) respectively. 'X' cross mark in blue indicates the positions where the resistive state measurements by the MIS system are taken. Time intervals where the MIS system detects a spike are represented in grey.

(g) and (h) Comparison of the spikes detected by the MIS and TMS system. The asterisk mark ('*') indicates the positions where the two systems agree and 'Φ' symbol discusses a specific case of discrepancy between the two systems.

The transient response of the target nano-device in response to the biased neural recording with time is illustrated in FIG. 20b. The device operates in a very high resistive state region of 1-1.5 MΩ. The spike detected from the MIS and TMS system were calculated to be 78, as shown in FIGS. 20c and d respectively. The response of the target device can be more closely scrutinized in FIGS. 20e and f which illustrates the neural recording and resistive state response of the DUT for time window 4 s-5 s in FIGS. 20a and b respectively. Marker 'x' is used to depict the resistive state measurements taken by the MIS system following the standard schematic as described in methods section and more clearly in FIG. 11. Notably, within the bin i.e. between two cross points the system is blind to the behaviour of the devices. However, the setting of the bin size in MIS platform is flexible and user-defined. One can choose to sample the read-outs more frequently and reduce the bin size in order to obtain higher accuracy in the timing resolution.

The memristive devices undergo a resistive drop in response to the supra-threshold events for instance in the first bin in FIG. 20f the resistive state of the device drops from approximately 1.3 MΩ to 1.15 M. The asterisk symbol '*' in FIG. 20g, h further confirms that the two systems agree for majority of instances. More specifically, the two systems agree for 13 instances from over 17 instances detected by the MIS system as shown in FIG. 20g. The symbol 'Φ' indicates an instance of mismatch between the two systems. Interestingly, at this instance MIS system detects a neural event which clearly looks like a spike, however, TMS fails to detect any spiking activity over here. On further careful examination of the neural recording it was observed that the TMS also fails to detect apparent spiking events at approximately 1.1 s, 1.6 s, 1.9 s, 2.2 s, 2.5 s, 2.7 s, 3.3 s, 3.6 s, 3.9 s some of which are detected by the MIS system (see FIG. 18). Besides, MIS system in FIG. 20g fails to detect spikes at 4.55 s, most likely due to inappropriate selection of gain and offset operational parameters. From these observations it can be safely concluded that although we assume TMS to be a perfect spike-detector for our experiments but in practical operation the case is not the same. Benchmarking of the detected spikes revealed a TPR and FPR of 70% and 13.7% respectively. Furthermore, measured results of thirteen different nano-devices with pre-processed neural recordings are recorded in Table 1 (FIG. 21). FIG. 18 depicts spikes detected by the Template Matching system. The bands depict the spikes detected. Notably, few instances where the TMS clearly fails to detect neural events are at approximately 1.1 s, 1.6 s, 1.9 s, 2.2 s, 2.5 s, 2.7 s, 3.3 s, 3.6 s, 3.9 s.

Receiver Operating Characteristics (sensitivity curve) that is rate of TP vs rate of FP for the measured devices of different dimensions are illustrated in FIG. 19a. FIGS. 19a and b depict a comparison of Receiver Operating Characteristics (ROC) that is rate of true positives vs rate of false positives for memristors of micro and nano dimensions. (a) The blue and red colour (marked BL and RE respectively) indicates the ROC curves for 60 μm×60 μm and 200 nm×200 nm devices respectively Symbol psi and circle in blue colour indicates different neural recordings with different spiking pattern used for the DUT. (b) Optimisation of spike detection capability for one of the 200 nm×200 nm device. Blue, red and green colour (marked by BL, RE and GR respectively) indicates the three different gain parameters i.e. 2.2, 2.4 and 2.6 respectively chosen for the experiment where the offset was kept constant at −0.6. For every gain the experiment was repeated five times. Asterisk symbol '*' indicates the average of the quantification parameters for each round of gain.

The details for the quantification parameters are presented in the Table 1 (FIG. 21). It can be evaluated that as the dimensions of the devices are reduced from 60 μm×60 μm to 200 nm×200 nm the detection accuracy of the system is reduced. One way for optimising the performance of the downscaled devices is to tune the gain and offset parameters to an optimum level. Therefore, one of the device was further tested with three different gain settings i.e. 2.2, 2.4 and 2.6 with a fixed offset setting at −0.6V as illustrated in FIG. 19b. For every round of gain, the experiment was repeated for five times and the details of the quantification parameters are illustrated in Table 2 (FIG. 22). The asterisk symbol, '*' represent the average of the quantification parameters for every round of gain. It can be interpreted that an improvement in the gain indicates an increase in rate of TP from 23.07% to 46.67% and these numbers in future can be further improved by estimating the optimum bin size for practical MIS implementation. Moreover, exploring different stacks of memristive devices with volatile characteristics might be another option to improve the performance of the devices, however, the main objective of optimised implementation of MIS technology with volatile metal-oxide devices is clearly illustrated.

Table 2 (FIG. 22) relates to optimisation of 200 nm×200 nm $TiO_x$ memristive devices. Gain and offset parameters for one of the 200 nm×200 nm device was optimised. Three different values of gain i.e. 2.2, 2.4 and 2.6 were used with constant offset values i.e. −0.6. For each round of gain the experiment was repeated five times. The quantification parameters for each round when benchmarked against the state-of-the-art template matching system are indicated in the illustrated table. MIS: Memristive Integrating Sensors System, TMS: Template matching system, TP: True Positives, FP: False Positives, TN: True Negatives, FN: False Negatives.

DISCUSSION

A major prerequisite in the implementation of fully implantable neural interfaces may be to develop electronic platforms capable of executing low-power on-site signal processing of the acquired neural activity. In this work, we experimentally demonstrated that scalable memristive devices can be ideally and more economically operated in the volatile region as MIS elements. The optimised performance is primarily due to the intrinsic resetting capability of the memristive devices in the volatile region eliminating or reducing the need for manually resetting the devices to its initial resistive state as is the case in non-volatile operating region The advantage lies in the fact that we immensely save on the power budget. Consider the example illustrated in FIGS. 16a and b, for a neural recording consisting of approximately 63 k data-points the target device is manually reset eleven times using a pulse of positive polarity of 100 μs pulse width. Realistically assuming +3V as the operating voltage and 10 kΩ as the resistive state of the device, the amount of power dissipated including the reset operation by the MIS system will be approximately equal to 3 mW per channel. The detailed power estimation methodology is presented in Supplementary Note 1. The reset operation consumes about 250 nJ of energy and 11 such resets for one neural recording would consume 2.7 mJ of energy which will be conserved in the volatile region.

Power is further retained in the volatile regime due to the operation of the devices in much higher resistive state region and to justify this consider the electrical characterisation results of nano-devices in FIGS. 3b and 5a. Assuming the operating resistive state and pulse width of the DUT to be 1 MΩ and 1 μs respectively, the amount of energy dissipated per channel can be estimated using the standard batch processing schematic. The read operation with standard read out voltage of +0.2V will be equal to 0.2 pJ (0.04 pJ multiplied by 5 reads per batch) and the write operation at 3V will cost 9 nJ (9 pJ multiplied by 1000 samples per batch). The average power dissipated per channel at 12.2 kHz as the sampling frequency can thus be estimated to be approximately 100 nW (see Supplementary Note 2). Voltage-time trade-off[46] can further assist in reducing the power dissipation by one order of magnitude, for instance, operating the same with 100 ns pulse width will further reduce the power dissipated to 10 nW per channel per device. However, the present measured results are already significantly lower than current state-of-the-art spike detectors projected at approximately 700 nW[25]. Naturally, system level application would include overheads such as memristor read-out and biasing circuitry, however, that discussion is not considered in the present work.

Furthermore, an important concern in the employability of the memristive devices is the recurrently observed device-to-device variable behaviour. To the advantage of the MIS platform since we estimate normalised changes in each bin instead of absolute changes the variability in devices is compensated to a large extent. Besides, the volatility characterisation module leads to automatic en-masse characterisation of the memristive devices and determines the safe region for the operation of devices in the volatile region. If higher and more invasive voltages are applied, the devices may switch to the non-volatile region and change their baseline operating region. The major focal point for building on the present work is to push the scaling limits for the employed devices towards 15 nm×15 nm[47] (according to the current state-of-the-art) along with optimised spike-detection capability. One of the possible reason affecting the spike-detection capability of the MIS system presently could be the longer self-reset duration of the $TiO_x$ devices which can be possibly countered by adjusting the bin-size or experimenting with different stack configuration of memristive devices demonstrating volatility[44]. On the other hand, these parameters will also crucially depend upon the specific application under study, for example, the amount of sensitivity required for a particular application.

The resistive state changes obtained in the output of the MIS platform are sensitive to the amplitude and polarity of the input neural signal thus preserving the richness of the signal and possibly opening the avenue for on-node spike-sorting[48]. Moreover, on the basis of these results, we presently envision a system level implementation of the MIS platform demonstrating strong potential for on-chip spike detection and sorting enhancing the state-of-the-art of present bio-electronics. In summary, we have demonstrated a novel concept for neural-spike detection using intrinsic volatile behaviour of metal-oxide memristive devices. Our results show the single nanoscale volatile devices are capable of identifying significant spiking activity in the input neural waveform in a highly power efficient way, thus paving the way towards advanced neuroprosthesis or applications such as bioelectronics medicines where the power dissipation remains as a major challenge.

Method Summary

Device Fabrication: The exemplary nano-devices exploited in this work, that is, $Ti/Pt/TiO_2/TiN$ (5/10/10/40 nm) may be fabricated as follow: 6-inch wafer was thermally oxidised to grow 200 nm $SiO_2$, which serves as an insulating layer. Then, direct write e-beam lithography method was adopted, using JEOL JBX 9300FS tool, to pattern the bottom electrodes (BEs) nanowires. Double layer resists were used to facilitate lift-off process of the BEs, which are constituted of 5 nm adhesive Ti layer and 10 nm Pt film. BEs were deposited using e-beam evaporation. Bottom access-electrodes (large features) were then defined via conventional photolithography patterning, e-beam evaporation of Ti/Au (5 nm/25 nm) and lift-off process. Access-electrodes connect the pads to the nanowires. To pattern the active layer, optical lithography, reactive sputtering and lift-off process were also used. 10 nm near-stoichiometric $TiO_2$ active layer was sputtered with Leybold Helios Pro XL Sputterer from Ti metal target. Next, 40 nm TiN top electrode (TEs) nanowires and 25 nm gold (Au) top access-electrodes were obtained in a similar way to the BEs and to the bottom access-electrodes, respectively. Except that the TiN film was deposited with Leybold Helios Pro XL Sputterer. On the other hand, micrometre sized devices exploited in this work were fabricated on top of $Si/SiO_2$ (200 nm) wafers. In each layer, three main patterning steps were processed, optical lithography, film deposition and lift-off process. For the first layer, 5 nm Ti and 10 nm Pt films were deposited via electron-beam evaporation to serve as BEs. In the second, magnetron reactive sputtering system was used to deposit the 25 nm near stoichiometric $TiO_2$ active film. In the final step, 10 nm Pt TEs were deposited using electron-beam evaporation system, as well. The final stack is constituted of $Ti/Pt/TiO_{2-x}/Pt$ (5/10/25/10 nm).

Figure 3:
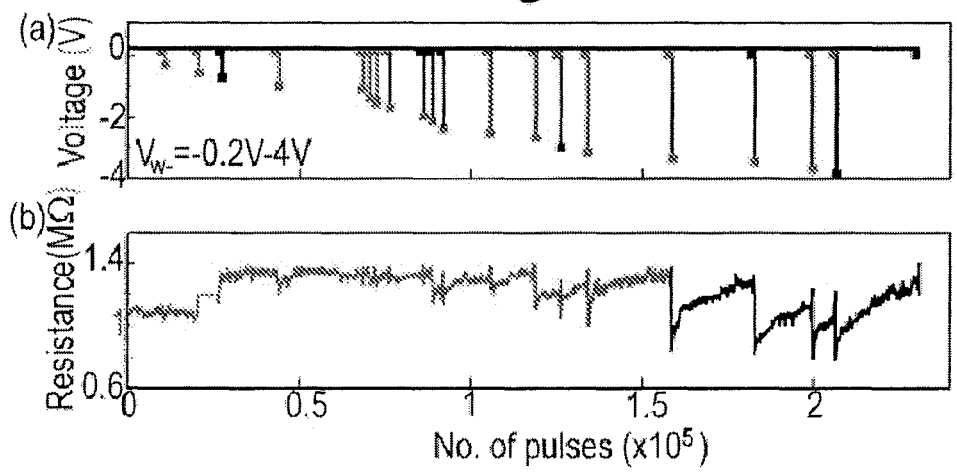
FIGS. 3a and 3b relate to electrical characterisation of an exemplary solid-state $TiO_x$ memristive devices in the volatile region.

Hardware Infrastructure/Instrumentation: The electrical characterisation in pulsing mode may be implemented using in-house fabricated electronic hardware infrastructure based on mBED LPC1768 micro-controller board[49,50] (FIGS. 3a and b, 5a, 7 and 10a). The customised instrument is capable of addressing single devices (up to 32) or devices fabricated in crossbar arrays of up to 1 kb in size (32×32 devices). The board is used to directly test the devices on-wafer interfaced using multi-channel probe card. The hardware platform is supported by custom-made Graphical User Interface (GUI) that permits device-by-device fully automated testing of the devices. The biasing schemes applied for read and write operations are the $V_r$ (FIG. 3 in reference[51]) and $V_{r/2}$ (FIG. 10b in reference[52]) schemes, which also helps in mitigating sneak-path effects.

Front-end neural recording system (CMOS Multi Electrode Array): In this work, neural activity was recorded from slices of dissected mid-peripheral rabbit retinal ganglion cells using an extended-CMOS technology[37] (FIGS. 10b-d). The CMOS based multi-transistor array (MEA) consists of 128×128 sensor sites which records the data at a sampling rate of 12.2 kHz and outputs a current time series containing approximately 63 k samples. The principle behind the operation of CMOS-MEA is as follows; the sensor sites may be insulated by an inert $TiO_2/ZrO_2$ layer and a thin metal layer beneath the oxide layer may be connected to the gate of the field-effect transistor. The voltage changes due to the interfaced neural tissue/cells above the recording sites are used for modulating the source-drain current in the MOSFET. Trans Impedance Amplifiers (TIA) fabricated on-chip converts the signal into voltage and amplifies the recorded signal from 0.1 mV-1 mV range to the 10-500 mV range. Importantly, this amplified signal is used as an input for the MIS. The CMOS MEA was kept external to the MIS platform and in this work the CMOS MEA is termed as the 'front-end' system.

Neural recording biasing strategy: The input to the MIS platform is the neural signal recorded from the MEA-based CMOS system[37] (see Methods, Front-end neural recording system and FIG. 10b-d), which corresponds to the output from the sensor 10. Each neural recording obtained contains approximately 63 k neural data points recorded at a sampling rate of 12.2 kHz. The neural recordings are in the range of ±0.5 V. The obtained data is pre-processed using the software-based gain and offset stage. This suitably amplified neural trace is then used to bias the memristive device using the customised hardware (FIG. 10a and FIG. 8) and the signal (equivalent to the output from the sensor 10) is fed to the target device in batches of 1000 data-points. In this work, we follow a standard schematic and in each batch, the resistive state of the device is assessed five times that is at the beginning of each batch, then after every 300 samples and finally at the end of each batch. Four consecutive measurements are thus obtained at $300^{th}$, $600^{th}$, $900^{th}$ and $1000^{th}$ data-point and one measurement is made at the end of each batch and before the beginning of next batch without any neural data point in between. This methodology transforms a batch of 1000 data-points in five bins and thus outputs a data compression rate of 200. Resistive state changes can be extracted from the consecutive measurements (bins) whist the measurement uncertainty (N) can be estimated from the measurements made at the end of each batch and the beginning of the next batch. Thus, for a single neural recording we obtain 316 resistive state measurements corresponding to 252 consecutive resistive state changes and 64 noise-level measurements. These resistive state changes help in estimating the threshold voltage of the target device consequently differentiating the significant resistive state changes from the insignificant ones (see FIG. 11, 12).

Neural signal processing through MIS platform: Estimation of the spikes detected by the MIS platform involves post-processing of the resistive state measurements. The normalised resistive state changes in each bin are plotted as a function of the highest voltage magnitude in each bin (see FIG. 13e and FIGS. 12a and b). In the volatile region of operation, all the noise measurements made in the positive polarity may be discarded. The noise measurements only in the negative polarity may be used to estimate the noise band boundaries. Absolute values of the noise measurements in the negative polarity are generated and then standard deviation (a) value is calculated. 4-sigma method that is μ (mean)±2σ is used and the noise band boundary is set as shown by the horizontal dashed line in FIG. 13e. All the resistive state changes outside this estimated boundary are considered to be significant whilst the resistive state changes falling within this band are considered as insignificant. These resistive state changes may be caused due to weak amplitude neural signals and cannot be differentiated from the noise measurements. On the other hand, if noise measurements in positive direction are included, estimation of mean and standard deviation values will be significantly affected leading to high probability of inclusion of noise. Moreover, for further clarity the comparison of the noise band setting in the volatile region with the non-volatile region is presented in FIGS. 12a and b. The noise band and the inherent threshold voltage divides the resistive state measurements in four parts and the data is quantified as follows: Outside the noise band and below $V_{th-}$: True Positives (TP), outside the noise band and above $V_{th-}$: False Positives (FP), inside the noise band and below $V_{th-}$: False Negatives (FN), inside the noise band and above $V_{th-}$: True Negatives (TN). These results are benchmarked against state-of-the-art TMS and these parameters are redefined. TP: agreement between the two systems for activity detected in a given bin. TN: means the two systems agree that there is no activity in a given bin, FP: MIS system detects activity whilst TMS system doesn't and FN: TMS system detects a spike whereas MIS system does not. Using these values, rate of TP (TPR) and FP (FPR) is determined using following equations:

$$\text{Rate of } TP = \frac{TP}{TP+FN}$$

$$\text{Rate of } TP = \frac{FP}{FP+TN}$$

Supplementary Material
Supplementary Note 1:
Estimation of Power Dissipated Per Channel Using Manual Frequent Method in FIGS. 16a and b (Non-Volatile Region).
Assumptions:
1) The following calculations have been done assuming the resistive state of the device to be 10 kΩ and series resistance (compliance) to be 1 kΩ.
2) The read voltage of the device is +0.5V and the write voltage is conservatively assumed to be +5V.
3) The pulse width used for the experiment is 100 μs.
4) For every batch of thousand data points, the state of the device is read five times.
5) P: Power, R: Resistance, V: Voltage, E: Energy, t: time (employed pulse width).
6) Sampling frequency is 12.2 kHz.

Energy Consumed for Read Operation:

$P=V^2/R=(0.5)^2/(1+10)$ kΩ=0.023 mW $E=P \times t=0.023$ mW×100 μs=2.3 nJ $E$ dissipated for 5 read operations=2.3 nJ×5=11.5 nJ Energy Consumed for Write Operation:

$P=V^2/R=(5)^2/(10)$ kΩ=2.5 mW $E=P \times t=2.5$ mW×100 μs=250 nJ

For 1000 samples, 1000×250 nJ=250 μJ

Resetting Operation Using One Single Pulse:

$E=2.5$ mW×100 μs=250 nJ

Average Power Consumption:
~3 mW.
Supplementary Note 2:
Estimation of Power Dissipated Per Channel in Volatile MIS Platform Using FIGS. 3a and b.
Assumptions:
1) The following calculations have been done assuming the resistive state of the device to be 1 MΩ and series resistance (compliance) to be 100 kΩ.
2) The read voltage of the device is +0.2V and the write voltage is conservatively assumed to be +3V.
3) The pulse width used for the experiment is 1 μs.
4) For every batch of thousand data points, the state of the device is read five times.
5) P: Power, R: Resistance, V: Voltage, E: Energy, t: time (employed pulse width).
6) Sampling frequency is 12.2 kHz.

Energy Consumed for Read Operation:

$P=V^2/R=(0.2)^2/(1$ MΩ+100 kΩ)=0.04 uW $E=P \times t=0.04$ uW×1 us=0.04 pJ.

$E$ dissipated for 5 read operations=0.04 pJ×5=0.2 pJ

Energy Consumed for Write Operation:

$P=V^2/R=(3)^2/(1)$ MΩ=9 uW $E=P \times t=9$uW×1 us=9 pJ.

For 1000 samples (per batch), 1000×9 pJ=9 nJ.

Average Power Consumption:

0.2 pJ+9 nJ/0.082=~100 nW.

Importantly, if the same experiment is performed with 100 ns pulses, the power consumption would be approximately 10 nW per batch.

Data Availability: The data that support the findings of this study are available from the corresponding author upon

REFERENCES

1. Buzsáki, G. Large-scale recording of neuronal ensembles. Nat. Neurosci. 7, 446-51 (2004).
2. Blanche, T. J., Spacek, M. A., Hetke, J. F., Swindale, N. V & Timothy, J. Polytrodes: High-Density Silicon Electrode Arrays for Large-Scale Multiunit Recording. J. Neural Eng. 93.5, 2987-3000 (2005).
3. Franke, F. et al. High-density microelectrode array recordings and real-time spike sorting for closed-loop experiments: an emerging technology to study neural plasticity. 6, 1-7 (2012).
4. Lambacher, A., Vitzthum, V., Zeitler, R. & Eickenscheidt, M., Eversmann, B., Thewes, R., Fromherz, P. Identifying firing mammalian neurons in networks with high-resolution multi-transistor array (MTA). Appl. Phys. A 102, 1-11 (2010).
5. Frey, U, Egert, U, Heer, F, Hafizovic, S. & Hierlemann, A. Microelectronic system for high-resolution mapping of extracellular electric fields applied to brain slices. Biosens. Bioelectron. 24, 2191-8 (2009).
6. HajjHassan, M., Chodavarapu, V. & Musallam, S. NeuroMEMS: Neural Probe Microtechnologies. Sensors 8, 6704-6726 (2008).
7. Lopez, C. M. et al. A 966-electrode neural probe with 384 configurable channels in 0.13 µm SOI CMOS. 2016 IEEE Int. Solid-State Circuits Conf. 392-393 (2016). doi: 10.1109/ISSCC.2016.7418072
8. Eversmann, Bjorn, Lambacher, Armin, Gerling, Thomas, Kunze, Alexander, Fromherz, Peter, Thewes, R. A neural tissue interfacing chip for in-vitro applications with 32 k recording/stimulation channels on an active area of 2.6 mm2. in 2011 Proceedings of the ESSCIRC (ESSCIRC) 211-214 (IEEE, 2011). doi:10.1109/ESSCIRC.2011.6044902
9. Gosselin, B. Recent advances in neural recording microsystems. Sensors 11, 4572-4597 (2011).
10. Hierlemann, A., Frey, U., Hafizovic, S. & Heer, F. Growing Cells Atop Microelectronic Chips: Interfacing Electrogenic Cells In Vitro With CMOS-Based Microelectrode Arrays. Proc. IEEE 99, 252-284 (2011).
11. Rey, H. G., Pedreira, C. & Quian Quiroga, R. Past, present and future of spike sorting techniques. Brain Res. Bull. 119, 106-117 (2015).
12. Lewicki, M. S. A review of methods for spike sorting: the detection and classification of neural action potentials classification of neural action potentials. Netw. Comput. Neural Syst. 9.4, R53-R78 (1998).
13. Schmidt, E. M. Computer separation of multi-unit neuroelectric data: A review. J. Neurosci. Methods 12, 95-111 (1984).
14. Quiroga, R. Q. Spike sorting. Curr. Biol. 22, R45-6 (2012).
15. Nicolelis, M. A. L. & Lebedev, M. A. Principles of neural ensemble physiology underlying the operation of brain-machine interfaces. Nat Rev Neurosci 10, 530-540 (2009).
16. Hatsopouplos, N. G. & Donoghue, J. P. The Science of Neural Interface Systems. Annu Rev Neurosci 32, 249-266 (2009).
17. Homer, M. & Nurmikko, A. Implants and decoding for intracortical brain computer interfaces. Annu. Rev. . . . 383-405 (2013). doi:10.1146/annurev-bioeng-071910-124640.Implants
18. Nicolas-Alonso, L. F. & Gomez-Gil, J. Brain computer interfaces, a review. Sensors (Basel). 12, 1211-79 (2012).
19. Navarro, X. et al. A Critical Review of Interfaces with the Peripheral Nervous System for the Control of Neuroprostheses and Hybrid Bionic Systems. J. Peripher. Nerv. Syst. 10, 229-258 (2005).
20. Wise, B. K. D. et al. Microelectrodes, Microelectronics, and Implantable Neural Microsystems. Proc. IEEE 96, 1184-1202 (2008).
21. Baranauskas, G. What limits the performance of current invasive brain machine interfaces? Front. Syst. Neurosci. 8, 68 (2014).
22. Stevenson, Ian HKording, K. P. How advances in neural recording affect data analysis. Nat. Neurosci. 14, 139-42 (2011).
23. Pedreira, C., Martinez, J., Ison, M. J. & Quian Quiroga, R. How many neurons can we see with current spike sorting algorithms? J. Neurosci. Methods 211, 58-65 (2012).
24. Eftekhar, A., Paraskevopoulou, S. E. & Constandinou, T. G. Towards a Next Generation Neural Interface: Optimizing Power, Bandwidth and Data Quality. 122-125 (2010).
25. Paraskevopoulou, S. E. & Constandinou, T. G. A sub-1 uW neural spike-peak detection and spike-count rate encoding circuit. in 2011 IEEE Biomedical Circuits and Systems Conference (BioCAS) 29-32 (IEEE, 2011). doi: 10.1109/BioCAS.2011.6107719
26. Prodromakis, T., Toumazou, C. & Chua, L. Two centuries of memristors. Nat. Mater. 11, 478-81 (2012).
27. Chua, L. & Sung Mo Kang. Memristive Devices and Systems. Proc. IEEE 64, 209-223 (1976).
28. Yang, J. J., Strukov, D. B. & Stewart, D. R. Memristive devices for computing. Nat. Nanotechnol. 8, 13-24 (2013).
29. Gupta, I., Serb, A., Khiat, A., Zeitler, R. & Vassanelli, S. Real-time coding and compression of neuronal spikes by metal-oxide memristors. Nat. Commun. (2016). doi: 10.1038/ncomms12805
30. Strukov, D. B. & Kohlstedt, H. Resistive switching phenomena in thin films: Materials, devices, and applications. MRS Bull. 37, 108-114 (2012).
31. Jeong, Doo Seok, Thomas, Reji, Katiyar, R S, Scott, J F, Kohlstedt, H, Petraru, A. & Hwang, C. S. Emerging memories: resistive switching mechanisms and current status. Reports Prog. Phys. 75, (2012).
32. Yu, S. et al. An Electronic Synapse Device Based on Metal Oxide Resistive Switching Memory for Neuromorphic Computation. 58, 2729-2737 (2011).
33. Linares-barranco, B. & Serrano-gotarredona, T. Memristance can explain Spike-Time-Dependent-Plasticity in Neural Synapses. Nat. Preced. (2009). doi:10101/npre.2009.3010.1
34. Prezioso, M., Merrikh-Bayat, F., Hoskins, B. D., Adam, G. C., Likharev, K. K. & Strukov, D. B. Training and operation of an integrated neuromorphic network based on metal-oxide memristors. Nature 521, 61-64 (2015).
35. Zeitler, R., Fromherz, P. & Zeck, G. Extracellular voltage noise probes the interface between retina and silicon chip. Appl. Phys. Lett. 99, 263702 (2011).
36. Zeck, G., Lambacher, A. & Fromherz, P. Axonal transmission in the retina introduces a small dispersion of relative timing in the ganglion cell population response. PLoS One 6, e20810 (2011).
37. Eversmann, Bjorn, Jenkner, Martin, Hofmann, Franz, Paulus, C., Brederlow, Ralf, Holzapfl, B., Fromherz, Peter, Merz, M. & Brenner, Markus, Schreiter, Matthias, Gabl, Reinhard, Plehnert, Kurt, Steinhauser, Michael, Eckstein, Gerald, Schmitt-landsiedel, Doris, Thewes, R. A 128×128 CMOS Biosensor Array for Extracellular Recording of Neural Activity. IEEE J. Solid-State Circuits 38, 2306-2317 (2003).
38. Gupta, I. et al. A Cell Classifier for RRAM Process Development. IEEE Trans. Circuits Syst. II Express Briefs 62, 676-680 (2015).
39. Gupta, I., Serb, A. & Khiat, A. Improving detection accuracy of memristor-based bio-signal sensing platform. IEEE Trans. Biomed. Circuits Syst. 1-9 (2016). doi: 10.1109/TBCAS.2016.2580499
40. Gupta, I., Serb, A., Khiat, A., Prodromakis, T. & Zeitler, R. Practical Operation Considerations for Memristive Integrating Sensors. Int. Symp. Circuits Syst. (2016).
41. Strukov, D. B. & Williams, R. S. Exponential ionic drift: Fast switching and low volatility of thin-film memristors. Appl. Phys. A Mater. Sci. Process. 94, 515-519 (2009).
42. Berdan, R. et al. Emulating short-term synaptic dynamics with memristive devices. Sci. Rep. 6, (2016).
43. Valov, I. et al. Nanobatteries in redox-based resistive switches require extension of memristor theory. Nat. Commun. 4, 1771 (2013).
44. Cortese, S., Trapatseli, M., Khiat, A. & Prodromakis, T. On the origin of resistive switching volatility in Ni/TiO2/Ni stacks. J. Appl. Phys. 120, 065104 (2016).
45. Gupta, I., Serb, A., Khiat, A., Zeitler, R. & Vassanelli, S. Real-time encoding and compression of neuronal spikes by metal-oxide memristors. Nat. Commun. 7, 1-16 (2016).
46. Xing, J., Serb, A., Berdan, R., Xui, H. & Prodromakis, T. An FPGA-based instrument for en-masse RRAM characterisation with ns pulsing resolution. IEEE Trans. Circuits Syst. I Regul. Pap. (2015).
47. Khiat, A., Ayliffe, P. & Prodromakis, T. High Density Crossbar Arrays with Sub-15 nm Single Cells via Liftoff Process Only. Sci. Rep. 6, 32614 (2016).
48. Gupta, I., Alexantrou, S., Khiat, A. & Prodromakis, T. Towards a memristor-based spike-sorting platform. 1-4
49. Serb, A., Berdan, R., Khiat, A., Papavassiliou, C. & Prodromakis, T. Live demonstration: A versatile, low-cost platform for testing large ReRAM cross-bar arrays. IEEE Int. Symp. CIRCUITS Syst. 9, 4799 (2014).
50. Serb, A., Khiat, A. & Prodromakis, T. An RRAM Biasing Parameter Optimizer. IEEE Trans. Electron Devices 62, 3685-3691 (2015).
51. Mustafa, J. & Waser, R. A Novel Reference Scheme for Reading Passive Resistive Crossbar Memories. IEEE Trans. Nanotechnol. 5, 687-691 (2006).
52. Seok, Jun Yeong, Song, Seul Ji, Yoon, Jung Ho, Yoon, Kyung Jean, Park, Tae Hyung, Kwon, D. E., Lim, Hyungkwang, Kim, G. H. & Jeong, Doo Seok, Hwang, C. S. A Review of Three-Dimensional Resistive Switching Cross-Bar Array Memories from the Integration and Materials Property Points of View. Adv. Funct. Mater. 24, 5316-5339 (2014).

The invention claimed is:

1. A method for detecting spikes in an input signal comprising:
applying an output from at least one sensor to a resistive switching component, wherein a voltage of the output varies depending on the input signal and wherein the resistive switching component is configured to undergo a volatile resistive state change from an initial resistive state to a further resistive state when a voltage with a magnitude less than or equal to a threshold value is applied across the resistive switching component, and the volatile resistive state change is such that the resistive switching component spontaneously relaxes from the further resistive state towards or beyond the initial resistive state after the magnitude of the voltage subsequently falls,
said applying the output from the at least one sensor results in the resistive switching component undergoing volatile resistive state changes;
sampling a further signal that is dependent on a resistance of the resistive switching component; and
identifying, using the sampled further signal, a sequence of volatile resistive state changes corresponding to spikes in the input signal.

2. The method of claim 1, further comprising applying an amplification and/or an offset to the output from the at least one sensor such that a majority of the spikes in the input signal result in a voltage with a magnitude less than or equal to the threshold value.

3. The method of claim 1, wherein the threshold value has a magnitude in the range of approximately 3.5V to 4.5V.

4. The method of claim 1, wherein the resistive switching component is configured to undergo a volatile resistive state change from an initial resistive state to a further resistive state when a voltage with a magnitude greater than or equal to a further threshold value is applied across the resistive switching component.

5. The method of claim 4, wherein the further threshold value has a magnitude in the range of approximately 0.6V to 2.4V.

6. The method of claim 1, wherein the sampling is carried out at equal intervals, preferably at a frequency higher than approximately 30 Hz.

7. The method of claim 1, wherein the sampling comprises monitoring the resistance of the resistive switching component and outputting when a portion of the further signal meets certain conditions.

8. The method of claim 1, wherein the resistive switching component is configured to operate in a range of resistances from approximately 0.1 MΩ to approximately 3 MΩ, or more preferably from approximately 0.7 MΩ to approximately 1.4 MΩ.

9. The method of claim 1, further comprising preparing the resistive switching component such that the resistive state change spontaneously relaxes from the further resistive state towards or beyond the initial resistive state after the magnitude of the voltage subsequently falls.

10. The method of claim 9, wherein the preparing comprises applying a series of progressively increasing voltage pulses until a non-volatile resistive state change occurs, such that the resistive switching component does not spontaneously relax from a further resistive state towards an initial resistive state after the magnitude of the voltage subsequently falls, and further comprises applying a further series of increasing voltage pulses until a volatile resistive state change is defined.

11. The method of claim 10, wherein the initial resistive state associated with the non-volatile resistive state change is greater than or equal to approximately 10 MΩ, and the further resistive state associated with the non-volatile resistive state change is less than approximately 10 MΩ, or preferably, the further resistive state associated with the non-volatile resistive state change is less than or equal to approximately 5 MΩ.

12. The method of claim 1, wherein identifying the volatile resistive state change corresponding to a spike comprises identifying a change in the further signal relative to a portion of the signal detected after a preceding spike, and determining that the change is greater than a predetermined value.

13. The method of claim 1, wherein the resistive switching component is configured to undergo a non-volatile resistive state change when a voltage with a magnitude above the magnitude of the threshold value is applied to the resistive switching component, wherein the non-volatile resistive state change is such that the resistive switching component does not spontaneously relax towards or beyond the initial resistive state after the magnitude of the voltage subsequently falls.

14. The method of claim 1, wherein the input signal is a biological signal, preferably, a neurological signal.

15. A system for detecting spikes in an input signal, comprising:
a resistive switching component configured to undergo a volatile resistive state change from an initial resistive state to a further resistive state when a voltage with a magnitude less than or equal to a threshold value is applied across the resistive switching component, and the volatile resistive state change is such that the resistive switching component spontaneously relaxes from the further resistive state towards or beyond the initial resistive state after the magnitude of the voltage subsequently falls, wherein the system is configured to apply, across the resistive switching component, a voltage such that the resistive switching component undergoes volatile resistive state changes when the voltage is applied wherein the voltage varies depending on the input signal; and
a processing unit configured to sample a further signal that is dependent on a resistance of the resistive switching component and identify, using the sampled further signal, a sequence of volatile resistive state changes corresponding to spikes in the input signal.

16. The system of claim 15, further comprising at least one sensor configured to measure the input signal and to output the voltage relating to the input signal.

* * * * *